US011065197B2

(12) United States Patent
Bernick et al.

(10) Patent No.: US 11,065,197 B2
(45) Date of Patent: *Jul. 20, 2021

(54) SOLUBLE ESTRADIOL CAPSULE FOR VAGINAL INSERTION

(71) Applicant: TherapeuticsMD, Inc., Boca Raton, FL (US)

(72) Inventors: Brian A. Bernick, Boca Raton, FL (US); Julia M. Amadio, Boca Raton, FL (US); Peter H. R. Persicaner, Boca Raton, FL (US); Thorsteinn Thorsteinsson, Boynton Beach, FL (US); Janice Louise Cacace, St. Petersburg, FL (US); Frederick D. Sancilio, Stuart, FL (US); Neda Irani, Palm Beach Gardens, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/837,929

(22) Filed: Apr. 1, 2020

(65) Prior Publication Data
US 2020/0352961 A1 Nov. 12, 2020

Related U.S. Application Data

(63) Continuation of application No. 14/649,818, filed as application No. PCT/US2013/046443 on Jun. 18, 2013, now abandoned.

(60) Provisional application No. 61/745,313, filed on Dec. 21, 2012.

(51) Int. Cl.
A61K 9/00 (2006.01)
A61K 31/565 (2006.01)
A61K 9/02 (2006.01)
A61K 9/107 (2006.01)
A61K 9/48 (2006.01)
A61K 31/57 (2006.01)
A61K 47/10 (2017.01)
A61K 47/14 (2017.01)
A61K 47/44 (2017.01)

(52) U.S. Cl.
CPC .............. A61K 9/0034 (2013.01); A61K 9/02 (2013.01); A61K 9/1075 (2013.01); A61K 9/48 (2013.01); A61K 9/4858 (2013.01); A61K 9/4866 (2013.01); A61K 31/565 (2013.01); A61K 31/57 (2013.01); A61K 47/10 (2013.01); A61K 47/14 (2013.01); A61K 47/44 (2013.01)

(58) Field of Classification Search
CPC ...... A61K 9/0034; A61K 31/565; A61K 9/02; A61K 47/44; A61K 9/48
See application file for complete search history.

(56) References Cited

U.S. PATENT DOCUMENTS

| 1,967,351 A | 1/1934 | Doisy |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Stein et al. |
| 3,526,648 A | 9/1970 | Bertin et al. |
| 3,710,795 A | 1/1973 | Higuchi et al. |
| 3,729,560 A | 4/1973 | Hagerman |
| 3,729,566 A | 4/1973 | Ericsson et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 7/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 4/1977 | Higuchi et al. |
| 4,071,623 A | 1/1978 | van der Vies |
| 4,093,709 A | 6/1978 | Choi et al. |
| 4,154,820 A | 5/1979 | Simoons |
| 4,155,991 A | 5/1979 | Schopflin et al. |
| 4,196,188 A | 4/1980 | Besins |
| 4,215,691 A | 8/1980 | Wong |

(Continued)

FOREIGN PATENT DOCUMENTS

| BR | P11001367-9 A2 | 7/2012 |
| CA | 2044371 A1 | 12/1991 |

(Continued)

OTHER PUBLICATIONS

US 6,214,374 B1, 04/2001, Schmirler et al. (withdrawn)
Gullapalli, "Soft Gelatin Capsules (Softgels)," Journal of Pharmaceutical Sciences, vol. 99, Issue 10, pp. 4107-4148 (Year: 2010).*
Abbas et al., Regression of endometrial implants treated with vitamin $D_3$ in a rat model of endometriosis, European J of Pharma, 715 (2013) 72-75, Elsevier.
Abitec, CapmulMCM, EP, Technical Data Sheet, version 10, 2014, Columbus, OH.
Abitec, CapmulMCM, NF, Technical Data Sheet, version 6, 2014, Columbus, OH.
Abitec, CapmulMCM, Saftey Data Sheet,2011, Janesville, WI.
Abitec, CapmulMCM, Technical Data Sheet, version 17, 2014, Columbus, OH.

(Continued)

Primary Examiner — Tracy Liu
(74) Attorney, Agent, or Firm — Sterne, Kessler, Goldstein & Fox P.L.L.C.

(57) ABSTRACT

According to various embodiments of this disclosure, pharmaceutical formulations comprising solubilized estradiol are provided. In various embodiments, such formulations are encapsulated in soft capsules which may be vaginally inserted for the treatment of vulvovaginal atrophy.

22 Claims, 2 Drawing Sheets

(56) References Cited

U.S. PATENT DOCUMENTS

| | | |
|---|---|---|
| 4,237,885 A | 12/1980 | Wong et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,043,331 A | 8/1991 | Hirvonen et al. |
| 5,059,426 A | 10/1991 | Chiang |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,164,416 A | 11/1992 | Nagai et al. |
| 5,208,225 A | 5/1993 | Boissonneault et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,295,945 A | 3/1994 | Miller |
| 5,340,584 A | 8/1994 | Spicer et al. |
| 5,340,585 A | 8/1994 | Pike et al. |
| 5,340,586 A | 8/1994 | Pike et al. |
| 5,362,497 A | 11/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,453,279 A | 9/1995 | Lee et al. |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmuller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Hoffmann et al. |
| 5,543,150 A | 8/1996 | Bologna et al. |
| 5,547,948 A | 8/1996 | Barcomb |
| 5,556,635 A | 9/1996 | Istin et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Mikler et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Teillaud et al. |
| 5,607,691 A | 3/1997 | Hale et al. |
| 5,607,693 A | 3/1997 | Bonte et al. |
| 5,609,617 A | 3/1997 | Shealy et al. |
| 5,620,705 A | 4/1997 | Dong et al. |
| 5,626,866 A | 5/1997 | Ebert et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,645,856 A | 7/1997 | Lacy et al. |
| 5,653,983 A | 8/1997 | Meybeck et al. |
| 5,656,286 A | 8/1997 | Miranda et al. |
| 5,660,839 A | 8/1997 | Allec et al. |
| 5,662,927 A | 9/1997 | Ehrlich et al. |
| 5,663,160 A | 9/1997 | Meybeck et al. |
| 5,676,968 A | 10/1997 | Lipp et al. |
| 5,677,292 A | 10/1997 | Li et al. |
| 5,686,097 A | 11/1997 | Taskovich et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Kanios et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Yewey et al. |
| 5,780,050 A | 7/1998 | Jain et al. |
| 5,788,980 A | 8/1998 | Nabahi |
| 5,788,984 A | 8/1998 | Guenther et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Hirano et al. |
| 5,827,200 A | 10/1998 | Caillouette |
| 5,840,327 A | 11/1998 | Gale et al. |
| 5,843,468 A | 12/1998 | Burkoth et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,869,084 A | 2/1999 | Paradissis et al. |
| 5,882,676 A | 3/1999 | Lee et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Lipp et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,942,531 A | 8/1999 | Diaz et al. |
| 5,952,000 A | 9/1999 | Venkateshwaran et al. |
| 5,958,446 A | 9/1999 | Miranda et al. |
| 5,962,445 A | 10/1999 | Stewart |
| 5,968,919 A | 10/1999 | Samour et al. |
| 5,972,372 A | 10/1999 | Saleh et al. |
| 5,985,311 A | 11/1999 | Cordes et al. |
| 5,985,850 A | 11/1999 | Falk et al. |
| 5,985,861 A | 11/1999 | Levine et al. |
| 5,989,568 A | 11/1999 | Breton et al. |
| 5,993,856 A | 11/1999 | Ragavan et al. |
| 6,001,846 A | 12/1999 | Edwards et al. |
| 6,007,835 A | 12/1999 | Bon Lapillonne et al. |
| 6,010,715 A | 1/2000 | Wick et al. |
| 6,013,276 A | 1/2000 | Math et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann |
| 6,039,968 A | 3/2000 | Nabahi |

(56) References Cited

U.S. PATENT DOCUMENTS

| | | |
|---|---|---|
| 6,040,340 A | 3/2000 | Chwalisz et al. |
| 6,056,972 A | 5/2000 | Hermsmeyer |
| 6,060,077 A | 5/2000 | Meignant |
| 6,068,853 A | 5/2000 | Giannos et al. |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 8/2000 | Lacy et al. |
| 6,106,848 A | 8/2000 | Preuilh et al. |
| 6,117,446 A | 9/2000 | Place |
| 6,117,450 A | 9/2000 | Dittgen et al. |
| 6,124,362 A | 9/2000 | Bradbury et al. |
| 6,133,251 A | 10/2000 | Dittgen et al. |
| 6,133,320 A | 10/2000 | Yallampalli et al. |
| 6,139,868 A | 10/2000 | Hoffmann |
| 6,139,873 A | 10/2000 | Hughes, Jr. et al. |
| 6,149,935 A | 11/2000 | Chiang et al. |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | de Haan et al. |
| 6,190,331 B1 | 2/2001 | Caillouette |
| 6,201,072 B1 | 3/2001 | Rathi et al. |
| 6,217,886 B1 | 4/2001 | Onyuksel et al. |
| 6,225,297 B1 | 5/2001 | Stockemann et al. |
| 6,227,202 B1 | 5/2001 | Matapurkar |
| 6,228,383 B1 | 5/2001 | Hansen et al. |
| 6,228,852 B1 | 5/2001 | Shaak |
| 6,242,509 B1 | 6/2001 | Berger et al. |
| 6,245,811 B1 | 6/2001 | Horrobin et al. |
| 6,262,115 B1 | 7/2001 | Guittard et al. |
| 6,267,984 B1 | 7/2001 | Beste et al. |
| 6,274,165 B1 | 8/2001 | Meconi et al. |
| 6,277,418 B1 | 8/2001 | Markaverich et al. |
| 6,283,927 B1 | 9/2001 | Caillouette |
| 6,284,263 B1 | 9/2001 | Place |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | de Ziegler et al. |
| 6,309,669 B1 | 10/2001 | Setterstrom et al. |
| 6,309,848 B1 | 10/2001 | Howett et al. |
| 6,312,703 B1 | 11/2001 | Orthoefer |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Bowman et al. |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Dunlop et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Rossi Montero et al. |
| 6,465,005 B1 | 10/2002 | Biali et al. |
| 6,465,006 B1 | 10/2002 | Zhang et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Meconi et al. |
| 6,526,980 B1 | 3/2003 | Tracy et al. |
| 6,528,094 B1 | 3/2003 | Savoir et al. |
| 6,531,149 B1 | 3/2003 | Kirstgen et al. |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Stewart et al. |
| 6,548,491 B2 | 4/2003 | Tanabe et al. |
| 6,551,611 B2 | 4/2003 | Elliesen et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | de Ziegler et al. |
| 6,599,519 B1 | 7/2003 | Seo et al. |
| 6,610,325 B1 | 8/2003 | Meignant et al. |
| 6,610,652 B2 | 8/2003 | Adams et al. |
| 6,610,670 B2 | 8/2003 | Blckensfeld et al. |
| 6,610,674 B1 | 8/2003 | Schreiber |
| 6,635,274 B1 | 10/2003 | Masiz et al. |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop et al. |
| 6,653,298 B2 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,664,296 B1 | 12/2003 | Meignant |
| 6,682,757 B1 | 1/2004 | Wright |
| 6,692,763 B1 | 2/2004 | Cummings et al. |
| 6,708,822 B1 | 3/2004 | Muni |
| 6,716,454 B2 | 4/2004 | Meignant et al. |
| 6,720,001 B2 | 4/2004 | Chen et al. |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim et al. |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Huebner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Eini et al. |
| 6,911,438 B2 | 6/2005 | Wright |
| 6,923,988 B2 | 8/2005 | Patel et al. |
| 6,924,274 B2 | 8/2005 | Lardy et al. |

(56) References Cited

U.S. PATENT DOCUMENTS

| | | |
|---|---|---|
| 6,932,983 B1 | 8/2005 | Straub et al. |
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Daniels et al. |
| 6,962,691 B1 | 11/2005 | Lulla et al. |
| 6,962,908 B2 | 11/2005 | AloBl et al. |
| 6,967,194 B1 | 11/2005 | Matsuo et al. |
| 6,974,569 B2 | 12/2005 | Dunlop et al. |
| 6,977,250 B2 | 12/2005 | Rodriguez |
| 6,978,945 B2 | 12/2005 | Wong et al. |
| 6,987,129 B2 | 1/2006 | Mak et al. |
| 6,995,149 B1 | 2/2006 | Endrikat et al. |
| 7,004,321 B1 | 2/2006 | Palm et al. |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,104 B2 | 4/2006 | Gray et al. |
| 7,030,157 B2 | 4/2006 | Ke et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf, III et al. |
| 7,094,228 B2 | 8/2006 | Zhang et al. |
| 7,097,853 B1 | 8/2006 | Garbe et al. |
| 7,101,342 B1 | 9/2006 | Caillouette |
| 7,105,573 B2 | 9/2006 | Krajcik et al. |
| 7,135,190 B2 | 11/2006 | Piao et al. |
| 7,153,522 B1 | 12/2006 | Ikeura et al. |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira et al. |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze et al. |
| 7,459,445 B2 | 12/2008 | Hill et al. |
| 7,465,587 B2 | 12/2008 | Imrich |
| 7,470,433 B2 | 12/2008 | Carrara et al. |
| 7,485,666 B2 | 2/2009 | Villanueva et al. |
| 7,497,855 B2 | 3/2009 | Ausiello et al. |
| 7,498,303 B2 | 3/2009 | Arnold et al. |
| 7,534,765 B2 | 5/2009 | Gregg et al. |
| 7,534,780 B2 | 5/2009 | Wyrwa et al. |
| 7,550,142 B2 | 6/2009 | Giles-Komar et al. |
| 7,563,565 B1 | 7/2009 | Matsuo et al. |
| 7,569,274 B2 | 8/2009 | Besse et al. |
| 7,572,779 B2 | 8/2009 | AloBl et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White et al. |
| 7,815,936 B2 | 10/2010 | Hasenzahl et al. |
| 7,815,949 B2 | 10/2010 | Cohen |
| 7,829,115 B2 | 11/2010 | Besins et al. |
| 7,829,116 B2 | 11/2010 | Griswold et al. |
| RE42,012 E | 12/2010 | Deaver et al. |
| 7,850,992 B2 | 12/2010 | Kim et al. |
| 7,854,753 B2 | 12/2010 | Kraft et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio et al. |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh Bennink et al. |
| 7,945,459 B2 | 5/2011 | Grace et al. |
| 7,960,368 B2 | 6/2011 | Nickisch et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Coelingh Bennink et al. |
| 8,071,729 B2 | 12/2011 | Giles-Komar et al. |
| 8,075,916 B2 | 12/2011 | Song et al. |
| 8,075,917 B2 | 12/2011 | Chung et al. |
| 8,076,317 B2 | 12/2011 | Kulmann |
| 8,076,319 B2 | 12/2011 | Leonard |
| 8,080,553 B2 | 12/2011 | Keith et al. |
| 8,088,605 B2 | 1/2012 | Beudet et al. |
| 8,096,940 B2 | 1/2012 | Josephson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernaes et al. |
| 8,124,595 B2 | 2/2012 | Boissonneault |
| 8,147,561 B2 | 4/2012 | Binmoeller |
| 8,148,546 B2 | 4/2012 | Schuster et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Watkinson et al. |
| 8,182,833 B2 | 5/2012 | Hermsmeyer |
| 8,187,615 B2 | 5/2012 | Friedman |
| 8,187,640 B2 | 5/2012 | Dunn |
| 8,195,403 B2 | 6/2012 | Ishikawa et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Thoene |
| 8,222,237 B2 | 7/2012 | Nickisch et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Vaya et al. |
| 8,268,806 B2 | 9/2012 | Labrie |
| 8,268,878 B2 | 9/2012 | Armer et al. |
| 8,273,730 B2 | 9/2012 | Fernandez et al. |
| 8,287,888 B2 | 10/2012 | Song et al. |
| 8,288,366 B2 | 10/2012 | Chochinov et al. |
| 8,318,898 B2 | 11/2012 | Fasel et al. |
| 8,324,193 B2 | 12/2012 | Lee Sepsick et al. |

(56) References Cited

U.S. PATENT DOCUMENTS

| | | |
|---|---|---|
| 8,329,680 B2 | 12/2012 | Evans et al. |
| 8,337,814 B2 | 12/2012 | Osbikken et al. |
| 8,344,007 B2 | 1/2013 | Tang et al. |
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Tamarkin et al. |
| 8,372,424 B2 | 2/2013 | Berry et al. |
| 8,372,806 B2 | 2/2013 | Bragagna et al. |
| 8,377,482 B2 | 2/2013 | Laurie et al. |
| 8,377,994 B2 | 2/2013 | Gray et al. |
| 8,394,759 B2 | 3/2013 | Barathur et al. |
| 8,415,332 B2 | 4/2013 | Diliberti et al. |
| 8,420,111 B2 | 4/2013 | Hermsmeyer |
| 8,435,561 B2 | 5/2013 | Besins et al. |
| 8,435,972 B2 | 5/2013 | Stein et al. |
| 8,449,879 B2 | 5/2013 | Laurent Applegate et al. |
| 8,450,108 B2 | 5/2013 | Boyce |
| 8,454,945 B2 | 6/2013 | Mccook et al. |
| 8,455,468 B2 | 6/2013 | Hoffman et al. |
| 8,461,138 B2 | 6/2013 | Boissonneault |
| 8,476,252 B2 | 7/2013 | Achleitner et al. |
| 8,481,488 B2 | 7/2013 | Carter |
| 8,486,374 B2 | 7/2013 | Tamarkin et al. |
| 8,486,442 B2 | 7/2013 | Matsushita et al. |
| 8,492,368 B2 | 7/2013 | Vanlandingham et al. |
| 8,507,467 B2 | 8/2013 | Matsui et al. |
| 8,512,693 B2 | 8/2013 | Capito et al. |
| 8,512,754 B2 | 8/2013 | Needham |
| 8,518,376 B2 | 8/2013 | Tamarkin et al. |
| 8,536,159 B2 | 9/2013 | Li et al. |
| 8,540,967 B2 | 9/2013 | Trivedi et al. |
| 8,541,400 B2 | 9/2013 | Johnsson et al. |
| 8,551,462 B2 | 10/2013 | Goldstein et al. |
| 8,551,508 B2 | 10/2013 | Lee et al. |
| 8,557,281 B2 | 10/2013 | Halliday et al. |
| 8,568,374 B2 | 10/2013 | De Graaff et al. |
| 8,591,951 B2 | 11/2013 | Kohn et al. |
| 8,613,951 B2 | 12/2013 | Zale et al. |
| 8,633,178 B2 | 1/2014 | Bernick et al. |
| 8,633,180 B2 | 1/2014 | Li et al. |
| 8,636,787 B2 | 1/2014 | Sabiria |
| 8,636,982 B2 | 1/2014 | Tamarkin et al. |
| 8,653,129 B2 | 2/2014 | Fein et al. |
| 8,658,627 B2 | 2/2014 | Voskuhl |
| 8,658,628 B2 | 2/2014 | Blucom |
| 8,663,681 B2 | 3/2014 | Ahmed et al. |
| 8,663,692 B1 | 3/2014 | Mueller et al. |
| 8,663,703 B2 | 3/2014 | Lerner et al. |
| 8,664,207 B2 | 3/2014 | Li et al. |
| 8,669,293 B2 | 3/2014 | Levy et al. |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Li et al. |
| 8,703,105 B2 | 4/2014 | Tamarkin et al. |
| 8,709,385 B2 | 4/2014 | Tamarkin et al. |
| 8,709,451 B2 | 4/2014 | Nam et al. |
| 8,715,735 B2 | 5/2014 | Funke et al. |
| 8,721,331 B2 | 5/2014 | Raghuprasad |
| 8,722,021 B2 | 5/2014 | Friedman et al. |
| 8,734,846 B2 | 5/2014 | Ali et al. |
| 8,735,381 B2 | 5/2014 | Podolski |
| 8,741,336 B2 | 6/2014 | Dipierro et al. |
| 8,741,373 B2 | 6/2014 | Bromley et al. |
| 8,753,661 B2 | 6/2014 | Gassner et al. |
| 8,784,882 B2 | 7/2014 | Mattern |
| 8,846,648 B2 | 9/2014 | Bernick et al. |
| 8,846,649 B2 | 9/2014 | Bernick et al. |
| 8,933,059 B2 | 1/2015 | Bernick et al. |
| 8,987,237 B2 | 3/2015 | Bernick et al. |
| 8,987,238 B2 | 3/2015 | Bernick et al. |
| 8,993,548 B2 | 3/2015 | Bernick et al. |
| 8,993,549 B2 | 3/2015 | Bernick et al. |
| 9,005,597 B2 | 4/2015 | Hansen et al. |
| 9,006,222 B2 | 4/2015 | Bernick et al. |
| 9,012,434 B2 | 4/2015 | Bernick et al. |
| 9,114,145 B2 | 8/2015 | Bernick et al. |
| 9,114,146 B2 | 8/2015 | Bernick et al. |
| 9,180,091 B2 | 11/2015 | Bernick et al. |
| 9,248,136 B2 | 2/2016 | Bernick et al. |
| 9,289,382 B2 | 3/2016 | Bernick et al. |
| 9,301,920 B2 | 4/2016 | Bernick et al. |
| 9,931,349 B2 | 4/2018 | Shadiack et al. |
| 10,052,386 B2 | 8/2018 | Bernick et al. |
| 10,098,894 B2 | 10/2018 | Amadio et al. |
| 10,206,932 B2 | 2/2019 | Bernick et al. |
| 10,258,630 B2 | 4/2019 | Mirkin et al. |
| 10,398,708 B2 | 9/2019 | Mirkin et al. |
| 10,471,072 B2 | 11/2019 | Bernick et al. |
| 10,568,891 B2 | 2/2020 | Mirkin et al. |
| 2001/0005728 A1 | 6/2001 | Guittard et al. |
| 2001/0009673 A1 | 7/2001 | Lipp et al. |
| 2001/0021816 A1 | 9/2001 | Caillouette |
| 2001/0023261 A1 | 9/2001 | Ryoo et al. |
| 2001/0027189 A1 | 10/2001 | Bennink et al. |
| 2001/0029357 A1 | 10/2001 | Bunt et al. |
| 2001/0031747 A1 | 10/2001 | de Ziegler et al. |
| 2001/0032125 A1 | 10/2001 | Bhan et al. |
| 2001/0034340 A1 | 10/2001 | Pickar |
| 2012/0269878 A2 | 10/2001 | Cantor et al. |
| 2001/0053383 A1 | 12/2001 | Miranda et al. |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik et al. |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik et al. |
| 2002/0119198 A1 | 8/2002 | Gao et al. |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Chwalisz et al. |
| 2002/0173510 A1 | 11/2002 | Levinson et al. |
| 2002/0193356 A1 | 12/2002 | Van Beek et al. |
| 2002/0193758 A1 | 12/2002 | Sandberg |
| 2002/0197286 A1 | 12/2002 | Brandman et al. |
| 2003/0003139 A1 | 1/2003 | Lipp et al. |
| 2003/0004145 A1 | 1/2003 | Leonard |
| 2003/0007994 A1 | 1/2003 | Bunt et al. |
| 2003/0027772 A1 | 2/2003 | Breton |
| 2003/0044453 A1 | 3/2003 | Dittgen et al. |
| 2003/0049307 A1 | 3/2003 | Gyurik |
| 2003/0064097 A1 | 4/2003 | Patel et al. |
| 2003/0064975 A1 | 4/2003 | Koch et al. |
| 2003/0072760 A1 | 4/2003 | SirBlsku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0078245 A1 | 4/2003 | Bennink et al. |
| 2003/0091620 A1 | 5/2003 | Fikstad et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Franke et al. |
| 2003/0113268 A1 | 6/2003 | Buenafae et al. |
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |

(56) References Cited

U.S. PATENT DOCUMENTS

| | | |
|---|---|---|
| 2003/0157157 A1 | 8/2003 | Luo et al. |
| 2003/0166509 A1 | 9/2003 | Bltycky et al. |
| 2003/0170295 A1 | 9/2003 | Kim et al. |
| 2003/0175329 A1 | 9/2003 | Azarnoff et al. |
| 2003/0175333 A1 | 9/2003 | Shefer et al. |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Berstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Caubel et al. |
| 2003/0225048 A1 | 12/2003 | Caubel et al. |
| 2003/0225050 A1 | 12/2003 | Eichardt et al. |
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki et al. |
| 2004/0043043 A1 | 3/2004 | Schlyter et al. |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou Chacra-Vernet et al. |
| 2004/0073024 A1 | 4/2004 | Metcalf, III et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini Eteve et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0147578 A1 | 7/2004 | Calvet |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Fernandez et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Deaver et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Morris et al. |
| 2005/0020552 A1 | 1/2005 | Aschkenasy et al. |
| 2005/0021009 A1 | 1/2005 | Massara et al. |
| 2005/0025833 A1 | 2/2005 | Aschkenasy et al. |
| 2005/0031651 A1 | 2/2005 | Gervais et al. |
| 2005/0042173 A1 | 2/2005 | Besse et al. |
| 2005/0042268 A1 | 2/2005 | Aschkenasy et al. |
| 2005/0048116 A1 | 3/2005 | Straub et al. |
| 2005/0054991 A1 | 3/2005 | Tobyn et al. |
| 2005/0079138 A1 | 4/2005 | Chickering, III et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobild et al. |
| 2005/0118272 A1 | 6/2005 | Besse et al. |
| 2005/0129756 A1 | 6/2005 | Podhaisky et al. |
| 2005/0152956 A1 | 7/2005 | Dudley |
| 2005/0153946 A1 | 7/2005 | Hirsh et al. |
| 2005/0164977 A1 | 7/2005 | Coelingh Bennink |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Popp et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Yang et al. |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 12/2005 | Jorda et al. |
| 2005/0266088 A1 | 12/2005 | Hinrichs et al. |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0014728 A1 | 1/2006 | Chwalisz et al. |
| 2006/0018937 A1 | 1/2006 | Friedman et al. |
| 2006/0019978 A1 | 1/2006 | Bllog |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0040904 A1 | 2/2006 | Ahmed et al. |
| 2006/0051391 A1 | 3/2006 | Dvoskin et al. |
| 2006/0052341 A1 | 3/2006 | Cornish et al. |
| 2006/0052799 A1* | 3/2006 | Middleman ............ A61B 17/10 606/114 |
| 2006/0069031 A1 | 3/2006 | Loumaye |
| 2006/0078618 A1 | 4/2006 | Constantinides et al. |
| 2006/0083778 A1 | 4/2006 | Allison et al. |
| 2006/0084704 A1 | 4/2006 | Shih et al. |
| 2006/0088580 A1 | 4/2006 | Meconi et al. |
| 2006/0089337 A1 | 4/2006 | Casper et al. |
| 2006/0093678 A1 | 5/2006 | Chickering, III et al. |
| 2006/0100180 A1 | 5/2006 | Bohlmann et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich |
| 2006/0134188 A1 | 6/2006 | Podhaisky et al. |
| 2006/0135619 A1 | 6/2006 | Kick et al. |
| 2006/0165744 A1 | 7/2006 | Jamil et al. |
| 2006/0193789 A1 | 8/2006 | Tamarkin et al. |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Brodbeck et al. |

(56) References Cited

U.S. PATENT DOCUMENTS

| | | |
|---|---|---|
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |
| 2006/0247221 A1 | 11/2006 | Coelingh Bennink et al. |
| 2006/0251581 A1 | 11/2006 | McIntyre et al. |
| 2006/0252049 A1 | 11/2006 | Shuler et al. |
| 2006/0257472 A1 | 11/2006 | Nielsen |
| 2006/0275218 A1 | 12/2006 | Tamarkin et al. |
| 2006/0275360 A1 | 12/2006 | Ahmed et al. |
| 2006/0276414 A1 | 12/2006 | Coelingh Bennink et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0292223 A1 | 12/2006 | Woolfson et al. |
| 2007/0004693 A1 | 1/2007 | Woolfson et al. |
| 2007/0004694 A1 | 1/2007 | Woolfson et al. |
| 2007/0009559 A1 | 1/2007 | Li et al. |
| 2007/0009594 A1 | 1/2007 | Grubb et al. |
| 2007/0010550 A1 | 1/2007 | McKenzie |
| 2007/0014839 A1 | 1/2007 | Bracht |
| 2007/0015698 A1 | 1/2007 | Kleinman et al. |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0036843 A1 | 2/2007 | Hirsh et al. |
| 2007/0037780 A1 | 2/2007 | Ebert et al. |
| 2007/0037782 A1 | 2/2007 | Hibino et al. |
| 2007/0042038 A1 | 2/2007 | Besse |
| 2007/0049567 A1 | 3/2007 | Wiley |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0071777 A1 | 3/2007 | Bromer et al. |
| 2007/0078091 A1 | 4/2007 | Hubler et al. |
| 2007/0088029 A1 | 4/2007 | Bllog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Gargiulo et al. |
| 2007/0154533 A1 | 7/2007 | Dudley |
| 2007/0167418 A1 | 7/2007 | Ferguson |
| 2007/0178166 A1 | 8/2007 | Bernstein et al. |
| 2007/0184558 A1 | 8/2007 | Roth et al. |
| 2007/0185068 A1 | 8/2007 | Ferguson et al. |
| 2007/0190022 A1 | 8/2007 | Chiao et al. |
| 2007/0191319 A1 | 8/2007 | Ke et al. |
| 2007/0191321 A1 | 8/2007 | Ahmed |
| 2007/0196415 A1 | 8/2007 | Chen et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Galey et al. |
| 2007/0238713 A1 | 10/2007 | Gast et al. |
| 2007/0243229 A1 | 10/2007 | Smith et al. |
| 2007/0248658 A1 | 10/2007 | Zurdo Schroeder et al. |
| 2007/0254858 A1 | 11/2007 | Cronk |
| 2007/0255197 A1 | 11/2007 | Humberstone et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0270394 A1 | 11/2007 | El-Alfy et al. |
| 2007/0281008 A1 | 12/2007 | Lin et al. |
| 2007/0286819 A1 | 12/2007 | DeVries et al. |
| 2007/0287688 A1 | 12/2007 | Chan et al. |
| 2007/0287789 A1 | 12/2007 | Jones et al. |
| 2007/0292359 A1 | 12/2007 | Friedman et al. |
| 2007/0292387 A1 | 12/2007 | Jon et al. |
| 2007/0292461 A1 | 12/2007 | Tamarkin et al. |
| 2007/0292493 A1 | 12/2007 | Brierre |
| 2007/0298089 A1 | 12/2007 | Saeki et al. |
| 2008/0026035 A1 | 1/2008 | Chollet et al. |
| 2008/0026040 A1 | 1/2008 | Farr et al. |
| 2008/0026062 A1 | 1/2008 | Farr et al. |
| 2008/0038219 A1 | 2/2008 | Carlson et al. |
| 2008/0038350 A1 | 2/2008 | Gerecke et al. |
| 2008/0039405 A1 | 2/2008 | Langley et al. |
| 2008/0050317 A1 | 2/2008 | Tamarkin et al. |
| 2008/0051351 A1 | 2/2008 | Ghisalberti |
| 2008/0063607 A1 | 3/2008 | Tamarkin et al. |
| 2008/0069779 A1 | 3/2008 | Tamarkin et al. |
| 2008/0069791 A1 | 3/2008 | Beissert |
| 2008/0085877 A1 | 4/2008 | Bortz |
| 2008/0095831 A1 | 4/2008 | McGraw |
| 2008/0095838 A1 | 4/2008 | Abou Chacra-Vernet |
| 2008/0113953 A1 | 5/2008 | De Vries et al. |
| 2008/0114050 A1 | 5/2008 | Fensome et al. |
| 2008/0119537 A1 | 5/2008 | Zhang et al. |
| 2008/0125402 A1 | 5/2008 | Diliberti |
| 2008/0138379 A1 | 6/2008 | Jennings-Spring |
| 2008/0138390 A1 | 6/2008 | Hsu et al. |
| 2008/0139392 A1 | 6/2008 | Acosta Zara et al. |
| 2008/0145423 A1 | 6/2008 | Khan et al. |
| 2008/0153789 A1 | 6/2008 | Dmowski et al. |
| 2008/0175814 A1 | 7/2008 | Phiasivongsa et al. |
| 2008/0175905 A1 | 7/2008 | Liu et al. |
| 2008/0175908 A1 | 7/2008 | Liu et al. |
| 2008/0188829 A1 | 8/2008 | Creasy |
| 2008/0206156 A1 | 8/2008 | Cronk |
| 2008/0206159 A1 | 8/2008 | Tamarkin et al. |
| 2008/0206161 A1 | 8/2008 | Tamarkin et al. |
| 2008/0214512 A1 | 9/2008 | Seitz et al. |
| 2008/0220069 A1 | 9/2008 | Allison |
| 2008/0226698 A1 | 9/2008 | Tang et al. |
| 2008/0227763 A1 | 9/2008 | Lanquetin et al. |
| 2008/0234199 A1 | 9/2008 | Katamreddy |
| 2008/0234240 A1 | 9/2008 | Duesterberg et al. |
| 2008/0255078 A1 | 10/2008 | Katamreddy |
| 2008/0255089 A1 | 10/2008 | Katamreddy |
| 2008/0261931 A1 | 10/2008 | Hedner et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson et al. |
| 2009/0010968 A1 | 1/2009 | Allart et al. |
| 2009/0011041 A1 | 1/2009 | Musaeva et al. |
| 2009/0017120 A1 | 1/2009 | Trimble et al. |
| 2009/0022683 A1 | 1/2009 | Song et al. |
| 2009/0047357 A1 | 2/2009 | Tomohira et al. |
| 2009/0053294 A1 | 2/2009 | Prendergast |
| 2009/0060982 A1 | 3/2009 | Ron et al. |
| 2009/0060997 A1 | 3/2009 | Seitz et al. |
| 2009/0068118 A1 | 3/2009 | Eini et al. |
| 2009/0074859 A1 | 3/2009 | Patel |
| 2009/0081206 A1 | 3/2009 | Leibovitz |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Liu et al. |
| 2009/0130029 A1 | 5/2009 | Tamarkin et al. |
| 2009/0131385 A1 | 5/2009 | Voskuhl |
| 2009/0136574 A1 | 5/2009 | Diaz-Astruc et al. |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin et al. |
| 2009/0181088 A1 | 7/2009 | Song et al. |
| 2009/0186081 A1 | 7/2009 | Holm et al. |
| 2009/0197843 A1 | 8/2009 | Notelovitz et al. |
| 2009/0203658 A1 | 8/2009 | Marx et al. |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy |
| 2009/0269403 A1 | 10/2009 | Shaked et al. |

(56) References Cited

U.S. PATENT DOCUMENTS

| | | |
|---|---|---|
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Liu et al. |
| 2009/0325916 A1 | 12/2009 | Zhang et al. |
| 2010/0008985 A1 | 1/2010 | Pellikaan et al. |
| 2010/0028360 A1 | 2/2010 | Atwood |
| 2010/0034838 A1 | 2/2010 | Staniforth et al. |
| 2010/0034880 A1 | 2/2010 | Sintov et al. |
| 2010/0040671 A1 | 2/2010 | Ahmed et al. |
| 2010/0048523 A1 | 2/2010 | Blchman et al. |
| 2010/0055138 A1 | 3/2010 | Margulies et al. |
| 2010/0074959 A1 | 3/2010 | Hansom et al. |
| 2010/0086501 A1 | 4/2010 | Chang et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Shenoy et al. |
| 2010/0143481 A1 | 6/2010 | Shenoy et al. |
| 2010/0150993 A1 | 6/2010 | Theobild et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh Bennink et al. |
| 2010/0190758 A1 | 7/2010 | Fauser et al. |
| 2010/0204326 A1 | 8/2010 | D Souza |
| 2010/0210994 A1 | 8/2010 | Zarif |
| 2010/0221195 A1 | 9/2010 | Tamarkin et al. |
| 2010/0227797 A1 | 9/2010 | Axelson et al. |
| 2010/0240626 A1 | 9/2010 | Kulkarni et al. |
| 2010/0247482 A1 | 9/2010 | Cui et al. |
| 2010/0247632 A1 | 9/2010 | Dong et al. |
| 2010/0247635 A1 | 9/2010 | Rosenberg et al. |
| 2010/0255085 A1 | 10/2010 | Liu et al. |
| 2010/0273730 A1 | 10/2010 | Hsu et al. |
| 2010/0278759 A1 | 11/2010 | Murad |
| 2010/0279988 A1 | 11/2010 | Setiawan et al. |
| 2010/0291191 A1 | 11/2010 | Shoichet et al. |
| 2010/0292199 A1 | 11/2010 | Leverd et al. |
| 2010/0303825 A9 | 12/2010 | SirBlsku |
| 2010/0312137 A1 | 12/2010 | Gilmour et al. |
| 2010/0316724 A1 | 12/2010 | Whitfield et al. |
| 2010/0322884 A1 | 12/2010 | Dipietro et al. |
| 2010/0330168 A1 | 12/2010 | Gicquel et al. |
| 2011/0028439 A1 | 2/2011 | Witt-Enderby et al. |
| 2011/0039814 A1 | 2/2011 | Huatan et al. |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland et al. |
| 2011/0091555 A1 | 4/2011 | De Luigi Bruschi et al. |
| 2011/0098258 A1 | 4/2011 | Masini Eteve et al. |
| 2011/0098631 A1 | 4/2011 | McIntyre et al. |
| 2011/0104268 A1 | 5/2011 | Pachot et al. |
| 2011/0104289 A1 | 5/2011 | Savoir Vilboeuf et al. |
| 2011/0130372 A1 | 6/2011 | Agostinacchio et al. |
| 2011/0135719 A1 | 6/2011 | Besins et al. |
| 2011/0142945 A1 | 6/2011 | Chen et al. |
| 2011/0152840 A1 | 6/2011 | Lee et al. |
| 2011/0158920 A1 | 6/2011 | Morley et al. |
| 2011/0171140 A1 | 7/2011 | Illum et al. |
| 2011/0182997 A1 | 7/2011 | Lewis et al. |
| 2011/0190201 A1 | 8/2011 | Hyde et al. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Bruno Raimondi et al. |
| 2011/0244043 A1 | 10/2011 | Xu et al. |
| 2011/0250256 A1 | 10/2011 | Hyun Oh et al. |
| 2011/0250259 A1 | 10/2011 | Buckman |
| 2011/0250274 A1 | 10/2011 | Shaked et al. |
| 2011/0256092 A1 | 10/2011 | Phiasivongsa et al. |
| 2011/0262373 A1 | 10/2011 | Umbert Millet |
| 2011/0262494 A1 | 10/2011 | Achleitner et al. |
| 2011/0268665 A1 | 11/2011 | Tamarkin et al. |
| 2011/0275584 A1 | 11/2011 | Wilckens et al. |
| 2011/0281832 A1 | 11/2011 | Li et al. |
| 2011/0287094 A1 | 11/2011 | Penhasi et al. |
| 2011/0293720 A1 | 12/2011 | General et al. |
| 2011/0294738 A1 | 12/2011 | Ren et al. |
| 2011/0300167 A1 | 12/2011 | Mcmurry et al. |
| 2011/0301087 A1 | 12/2011 | Mcbride et al. |
| 2011/0306579 A1 | 12/2011 | Stein |
| 2011/0311592 A1 | 12/2011 | BirBlra |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De Groote |
| 2012/0015350 A1 | 1/2012 | NaBltiyan et al. |
| 2012/0021041 A1 | 1/2012 | Rossi et al. |
| 2012/0028888 A1 | 2/2012 | Janz et al. |
| 2012/0028910 A1 | 2/2012 | Takruri et al. |
| 2012/0028936 A1 | 2/2012 | Gloger et al. |
| 2012/0045532 A1 | 2/2012 | Cohen |
| 2012/0046264 A1 | 2/2012 | Simes et al. |
| 2012/0046518 A1 | 2/2012 | Yoakum et al. |
| 2012/0052077 A1 | 3/2012 | Truitt, III et al. |
| 2012/0058171 A1 | 3/2012 | De Graaff et al. |
| 2012/0058962 A1 | 3/2012 | Cumming et al. |
| 2012/0058979 A1 | 3/2012 | Keith et al. |
| 2012/0064135 A1 | 3/2012 | Levin et al. |
| 2012/0065179 A1 | 3/2012 | Andersson |
| 2012/0065221 A1 | 3/2012 | Blbul |
| 2012/0087872 A1 | 4/2012 | Tamarkin et al. |
| 2012/0101073 A1 | 4/2012 | Mannion et al. |
| 2012/0121517 A1 | 5/2012 | Song et al. |
| 2012/0121692 A1 | 5/2012 | Xu et al. |
| 2012/0122829 A1 | 5/2012 | Taravella et al. |
| 2012/0128625 A1 | 5/2012 | Shalwitz et al. |
| 2012/0128654 A1 | 5/2012 | Terpstra et al. |
| 2012/0128683 A1 | 5/2012 | Shantha |
| 2012/0128733 A1 | 5/2012 | Perrin et al. |
| 2012/0128777 A1 | 5/2012 | Keck et al. |
| 2012/0129773 A1 | 5/2012 | Geier et al. |
| 2012/0129819 A1 | 5/2012 | Vancaillie et al. |
| 2012/0136013 A1 | 5/2012 | Li et al. |
| 2012/0142645 A1 | 6/2012 | Marx |
| 2012/0148670 A1 | 6/2012 | Kim et al. |
| 2012/0149748 A1 | 6/2012 | Shanler et al. |
| 2012/0172343 A1 | 7/2012 | Lindenthal et al. |
| 2012/0184515 A1 | 7/2012 | Klar et al. |
| 2012/0231052 A1 | 9/2012 | Sitruk Ware et al. |
| 2012/0232011 A1 | 9/2012 | Kneissel et al. |
| 2012/0232042 A1 | 9/2012 | Klar et al. |
| 2012/0263679 A1 | 10/2012 | Marlow et al. |
| 2012/0269721 A1 | 10/2012 | Weng et al. |
| 2012/0277249 A1 | 11/2012 | Andersson et al. |
| 2012/0277727 A1 | 11/2012 | Doshi et al. |
| 2012/0283671 A1 | 11/2012 | ShiBlta et al. |
| 2012/0295911 A1 | 11/2012 | Mannion et al. |
| 2012/0301517 A1 | 11/2012 | Zhang et al. |
| 2012/0301538 A1 | 11/2012 | Gordon Beresford et al. |
| 2012/0302535 A1 | 11/2012 | Caufriez et al. |
| 2012/0316130 A1 | 12/2012 | Hendrix |
| 2012/0316496 A1 | 12/2012 | Hoffmann et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0329738 A1 | 12/2012 | Liu |
| 2013/0004619 A1 | 1/2013 | Chow et al. |
| 2013/0011342 A1 | 1/2013 | Tamarkin et al. |
| 2013/0017239 A1 | 1/2013 | Viladot Petit et al. |
| 2013/0022674 A1 | 1/2013 | Dudley et al. |
| 2013/0023505 A1 | 1/2013 | Garfield et al. |
| 2013/0023823 A1 | 1/2013 | Simpson et al. |

(56) References Cited

U.S. PATENT DOCUMENTS

| | | |
|---|---|---|
| 2013/0028850 A1 | 1/2013 | Tamarkin et al. |
| 2013/0029947 A1 | 1/2013 | Nachaegari et al. |
| 2013/0029957 A1 | 1/2013 | Giliyar et al. |
| 2013/0045266 A1 | 2/2013 | Choi et al. |
| 2013/0045953 A1 | 2/2013 | Sitruk Ware et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Li et al. |
| 2013/0089574 A1 | 4/2013 | Schmidt Gollwitzer et al. |
| 2013/0090318 A1 | 4/2013 | Ulmann et al. |
| 2013/0102781 A1 | 4/2013 | Bevill et al. |
| 2013/0108551 A1 | 5/2013 | Langereis et al. |
| 2013/0116215 A1 | 5/2013 | Coma et al. |
| 2013/0116222 A1 | 5/2013 | Arnold et al. |
| 2013/0122051 A1 | 5/2013 | Abidi et al. |
| 2013/0123175 A1 | 5/2013 | Hill et al. |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Pakkalin et al. |
| 2013/0131028 A1 | 5/2013 | Snyder et al. |
| 2013/0131029 A1 | 5/2013 | Biltussen et al. |
| 2013/0149314 A1 | 6/2013 | Bullerdiek et al. |
| 2013/0150334 A1 | 6/2013 | Sun et al. |
| 2013/0164225 A1 | 6/2013 | Tamarkin et al. |
| 2013/0164346 A1 | 6/2013 | Lee et al. |
| 2013/0165744 A1 | 6/2013 | Carson et al. |
| 2013/0178452 A1 | 7/2013 | King |
| 2013/0183254 A1 | 7/2013 | Zhou et al. |
| 2013/0183325 A1 | 7/2013 | Bottoni et al. |
| 2013/0189193 A1 | 7/2013 | Tamarkin et al. |
| 2013/0189196 A1 | 7/2013 | Tamarkin et al. |
| 2013/0189230 A1 | 7/2013 | Shoichet et al. |
| 2013/0189368 A1 | 7/2013 | Mosqueira et al. |
| 2013/0210709 A1 | 8/2013 | Mcmurry et al. |
| 2013/0216550 A1 | 8/2013 | Penninger et al. |
| 2013/0216596 A1 | 8/2013 | Viladot Petit et al. |
| 2013/0224177 A1 | 8/2013 | Kim et al. |
| 2013/0224257 A1 | 8/2013 | Sah et al. |
| 2013/0224268 A1 | 8/2013 | Alam et al. |
| 2013/0224300 A1 | 8/2013 | Maggio |
| 2013/0225412 A1 | 8/2013 | Sardari Lodriche et al. |
| 2013/0225542 A1 | 8/2013 | Poegh et al. |
| 2013/0226113 A1 | 8/2013 | Schumacher et al. |
| 2013/0243696 A1 | 9/2013 | Wang et al. |
| 2013/0245253 A1 | 9/2013 | Marx et al. |
| 2013/0245570 A1 | 9/2013 | Jackson |
| 2013/0261096 A1 | 10/2013 | Merian et al. |
| 2013/0266645 A1 | 10/2013 | Becker et al. |
| 2013/0267485 A1 | 10/2013 | Da Silva Maia Filho |
| 2013/0273167 A1 | 10/2013 | Lee et al. |
| 2013/0274211 A1 | 10/2013 | Burman et al. |
| 2013/0280213 A1 | 10/2013 | Voskuhl |
| 2013/0316374 A1 | 11/2013 | Penninger et al. |
| 2013/0317065 A1 | 11/2013 | Tatani et al. |
| 2013/0317315 A1 | 11/2013 | Lu et al. |
| 2013/0324565 A1 | 12/2013 | Li et al. |
| 2013/0331363 A1 | 12/2013 | Li et al. |
| 2013/0338122 A1 | 12/2013 | Bernick et al. |
| 2013/0338123 A1 | 12/2013 | Bernick et al. |
| 2013/0338124 A1 | 12/2013 | Li et al. |
| 2013/0345187 A1 | 12/2013 | Rodriguez Oquendo |
| 2014/0018335 A1 | 1/2014 | Tatani et al. |
| 2014/0024590 A1 | 1/2014 | Weidhaas et al. |
| 2014/0031289 A1 | 1/2014 | Song et al. |
| 2014/0031323 A1 | 1/2014 | Perez |
| 2014/0066416 A1 | 3/2014 | Leunis et al. |
| 2014/0072531 A1 | 3/2014 | Kim et al. |
| 2014/0079686 A1 | 3/2014 | Prouty et al. |
| 2014/0088051 A1 | 3/2014 | Bernick et al. |
| 2014/0088058 A1 | 3/2014 | Maurizio |
| 2014/0088059 A1 | 3/2014 | Perumal et al. |
| 2014/0094426 A1 | 4/2014 | Drummond et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Bernick et al. |
| 2014/0113889 A1 | 4/2014 | Connor et al. |
| 2014/0127185 A1 | 5/2014 | Stein et al. |
| 2014/0127280 A1 | 5/2014 | Duesterberg et al. |
| 2014/0127308 A1 | 5/2014 | Opara et al. |
| 2014/0128798 A1 | 5/2014 | Janson et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Li et al. |
| 2014/0206616 A1 | 7/2014 | Ko et al. |
| 2014/0213565 A1 | 7/2014 | Bernick et al. |
| 2014/0329783 A1 | 11/2014 | Bernick et al. |
| 2014/0370084 A1 | 12/2014 | Bernick et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0133421 A1 | 5/2015 | Bernick et al. |
| 2015/0148323 A1 | 5/2015 | Bernick et al. |
| 2015/0164789 A1 | 6/2015 | Bernick et al. |
| 2015/0224117 A1 | 8/2015 | Bernick et al. |
| 2015/0224118 A1 | 8/2015 | Bernick et al. |
| 2015/0297733 A1 | 10/2015 | Oberegger et al. |
| 2015/0302435 A1 | 10/2015 | Bernick et al. |
| 2015/0342963 A1 | 12/2015 | Bernick et al. |
| 2015/0352126 A1 | 12/2015 | Bernick et al. |
| 2015/0359737 A1 | 12/2015 | Bernick et al. |
| 2016/0030449 A1 | 2/2016 | Persicaner et al. |
| 2016/0213685 A1 | 7/2016 | Bernick et al. |
| 2017/0056418 A1 | 3/2017 | Thorsteinsson et al. |
| 2017/0216310 A1 | 8/2017 | Mirkin et al. |
| 2017/0281645 A1 | 10/2017 | Shadiack et al. |
| 2017/0281646 A1 | 10/2017 | Inskeep et al. |
| 2017/0281647 A1 | 10/2017 | Shadiack et al. |
| 2017/0281776 A1 | 10/2017 | Shadiack et al. |
| 2018/0161343 A1 | 6/2018 | Mirkin et al. |
| 2018/0161344 A1 | 6/2018 | Mirkin et al. |
| 2018/0161345 A1 | 6/2018 | Bernick et al. |
| 2018/0221389 A1 | 8/2018 | Amadio et al. |
| 2018/0256598 A1 | 9/2018 | Mirkin et al. |
| 2018/0280410 A1 | 10/2018 | Amadio et al. |
| 2018/0289723 A1 | 10/2018 | Bernick et al. |
| 2019/0022107 A1 | 1/2019 | Mirkin et al. |
| 2019/0046542 A1 | 2/2019 | Bernick et al. |
| 2019/0070197 A1 | 3/2019 | Amadio et al. |
| 2019/0142844 A1 | 5/2019 | Bernick et al. |
| 2019/0247401 A1 | 8/2019 | Amadio et al. |
| 2019/0343771 A1 | 11/2019 | Mirkin et al. |
| 2019/0343845 A1 | 11/2019 | Bernick et al. |
| 2019/0358243 A1 | 11/2019 | Mirkin et al. |
| 2020/0069700 A1 | 3/2020 | Bernick et al. |

FOREIGN PATENT DOCUMENTS

| | | |
|---|---|---|
| CA | 2612380 | 12/2006 |
| CN | 102258455 A | 11/2011 |
| EP | 0261429 A1 | 3/1988 |
| EP | 275716 A1 | 7/1988 |
| EP | 0279977 A2 | 8/1988 |
| EP | 622075 A1 | 11/1994 |
| EP | 785211 A1 | 7/1997 |
| EP | 785212 A1 | 7/1997 |
| EP | 811381 A1 | 12/1997 |
| EP | 0904064 A1 | 3/1999 |
| EP | 0813412 B1 | 12/1999 |
| EP | 0750495 B1 | 12/2002 |
| EP | 1300152 A1 | 4/2003 |
| EP | 1094781 B1 | 7/2008 |
| EP | 2191833 A1 | 6/2010 |

(56) References Cited

FOREIGN PATENT DOCUMENTS

| | | |
|---|---|---|
| GB | 452238 A | 8/1936 |
| GB | 720561 A | 12/1954 |
| GB | 848881 A | 9/1960 |
| GB | 874368 A | 8/1961 |
| GB | 1589946 A | 5/1981 |
| IN | 2005KOL00053 | 8/2005 |
| IN | 216026 | 3/2008 |
| IN | 244217 | 11/2010 |
| JP | H4-503810 | 9/1990 |
| JP | H2-264725 A | 10/1990 |
| JP | 2002 510336 A | 4/2002 |
| JP | 2006 513182 A | 4/2006 |
| RU | 2155582 C2 | 9/2000 |
| WO | 199010425 A1 | 9/1990 |
| WO | 1990011064 | 10/1990 |
| WO | 1993017686 | 9/1993 |
| WO | 1994022426 | 10/1994 |
| WO | 1995005807 | 3/1995 |
| WO | 1995030409 | 11/1995 |
| WO | 1996009826 | 4/1996 |
| WO | 1996019975 | 7/1996 |
| WO | 1996030000 | 10/1996 |
| WO | 1997005491 | 2/1997 |
| WO | 1997040823 A1 | 11/1997 |
| WO | 1997043989 | 11/1997 |
| WO | 1998010293 | 3/1998 |
| WO | 1998032465 | 7/1998 |
| WO | WO 1998041217 A1 | 9/1998 |
| WO | 1998051280 | 11/1998 |
| WO | 199922680 A1 | 5/1999 |
| WO | 1999032072 | 7/1999 |
| WO | 1999039700 | 8/1999 |
| WO | 1999042109 | 8/1999 |
| WO | 1999043304 | 9/1999 |
| WO | 1999048477 | 9/1999 |
| WO | 1999052528 A1 | 10/1999 |
| WO | 1999053910 | 10/1999 |
| WO | WO 1999055333 A1 | 11/1999 |
| WO | 1999062497 A1 | 12/1999 |
| WO | 1999063974 | 12/1999 |
| WO | 2000001351 | 1/2000 |
| WO | 2000006175 | 2/2000 |
| WO | 2000038659 | 6/2000 |
| WO | 2000045795 | 8/2000 |
| WO | 2000050007 | 8/2000 |
| WO | 2000059577 | 10/2000 |
| WO | 2000076522 | 12/2000 |
| WO | 2001037808 | 5/2001 |
| WO | 2001054699 | 8/2001 |
| WO | 2001060325 | 8/2001 |
| WO | 2001087276 A1 | 11/2001 |
| WO | 2001091757 | 12/2001 |
| WO | 2002007700 | 1/2002 |
| WO | 2002011768 | 2/2002 |
| WO | 2002022132 | 3/2002 |
| WO | 2002040008 | 5/2002 |
| WO | 2002041878 | 5/2002 |
| WO | 2002053131 | 7/2002 |
| WO | 2002078602 | 10/2002 |
| WO | 2002078604 | 10/2002 |
| WO | 2003028667 | 4/2003 |
| WO | 2003041718 | 5/2003 |
| WO | 2003041741 | 5/2003 |
| WO | 2003068186 | 8/2003 |
| WO | 2003077923 | 9/2003 |
| WO | 2003082254 | 10/2003 |
| WO | 2003092588 | 11/2003 |
| WO | 2004014397 A1 | 2/2004 |
| WO | 2004014432 | 2/2004 |
| WO | 2004017983 | 3/2004 |
| WO | 2004032897 | 4/2004 |
| WO | WO 2004032942 A1 | 4/2004 |
| WO | 2004052336 | 6/2004 |
| WO | 2004054540 | 7/2004 |
| WO | 2004054576 A1 | 7/2004 |
| WO | 2004080413 | 9/2004 |
| WO | 2004105694 A2 | 12/2004 |
| WO | 2004110402 A1 | 12/2004 |
| WO | 2004110408 A2 | 12/2004 |
| WO | 2005027911 | 3/2005 |
| WO | 2005030175 | 4/2005 |
| WO | 2005081825 | 9/2005 |
| WO | 2005087194 | 9/2005 |
| WO | 2005087199 | 9/2005 |
| WO | 2005105059 | 11/2005 |
| WO | 2005115335 | 12/2005 |
| WO | 2005120470 | 12/2005 |
| WO | 2005120517 | 12/2005 |
| WO | 2006013369 | 2/2006 |
| WO | 2006034090 | 3/2006 |
| WO | 2006036899 | 4/2006 |
| WO | 2006053172 | 5/2006 |
| WO | 2006105615 | 10/2006 |
| WO | 2006113505 | 10/2006 |
| WO | 2006138686 | 12/2006 |
| WO | 2006138735 | 12/2006 |
| WO | 2007045027 | 4/2007 |
| WO | WO 2007076144 A2 | 7/2007 |
| WO | 2007103294 | 9/2007 |
| WO | 2007120868 | 10/2007 |
| WO | 2007123790 | 11/2007 |
| WO | 2007124250 | 11/2007 |
| WO | 2007144151 | 12/2007 |
| WO | 2008049516 | 5/2008 |
| WO | 2008152444 | 12/2008 |
| WO | 2009002542 | 12/2008 |
| WO | 2009036311 | 3/2009 |
| WO | 2009040818 | 4/2009 |
| WO | 2009069006 | 6/2009 |
| WO | 2009098072 | 8/2009 |
| WO | 2009133352 | 11/2009 |
| WO | 2010033188 | 3/2010 |
| WO | 2010146872 | 12/2010 |
| WO | 2011000210 | 1/2011 |
| WO | 2011073995 | 6/2011 |
| WO | 2011120084 | 10/2011 |
| WO | 2011128336 | 10/2011 |
| WO | 2012009778 | 1/2012 |
| WO | 2012024361 | 2/2012 |
| WO | 2012055814 A1 | 5/2012 |
| WO | 2012055840 A1 | 5/2012 |
| WO | 2012065740 | 5/2012 |
| WO | 2012098090 A1 | 7/2012 |
| WO | 2012116277 A1 | 8/2012 |
| WO | 2012118563 A2 | 9/2012 |
| WO | 2012120365 A1 | 9/2012 |
| WO | 2012127501 A2 | 9/2012 |
| WO | 2012156822 A1 | 11/2012 |
| WO | 2012158483 A2 | 11/2012 |
| WO | 20012156561 A1 | 11/2012 |
| WO | 2012166909 A1 | 12/2012 |
| WO | 2012170578 A1 | 12/2012 |
| WO | 2013011501 A1 | 1/2013 |
| WO | 2013025449 A1 | 2/2013 |
| WO | 2013028639 A1 | 2/2013 |
| WO | 2013035101 A1 | 3/2013 |
| WO | 2013044067 A1 | 3/2013 |
| WO | 2013045404 A2 | 4/2013 |
| WO | 2013059285 A1 | 4/2013 |
| WO | 2013063279 A1 | 5/2013 |
| WO | 2013064620 A1 | 5/2013 |
| WO | 2013071281 A1 | 5/2013 |
| WO | WO 2013078422 A2 | 5/2013 |
| WO | 2013088254 | 6/2013 |
| WO | 2013102665 A1 | 7/2013 |
| WO | 2013106437 A1 | 7/2013 |
| WO | 2013113690 | 8/2013 |
| WO | 2013124415 A1 | 8/2013 |
| WO | WO 2013112947 A1 | 8/2013 |
| WO | 2013127727 A1 | 9/2013 |
| WO | 2013127728 A1 | 9/2013 |
| WO | 2013144356 A1 | 10/2013 |
| WO | 2013149258 A2 | 10/2013 |
| WO | 2013158454 A2 | 10/2013 |

(56) References Cited

FOREIGN PATENT DOCUMENTS

| | | |
|---|---|---|
| WO | 2013170052 A1 | 11/2013 |
| WO | 2013178587 A1 | 12/2013 |
| WO | 2013181449 A1 | 12/2013 |
| WO | 2013192248 | 12/2013 |
| WO | 2013192249 | 12/2013 |
| WO | 2013192250 | 12/2013 |
| WO | 2013192251 | 12/2013 |
| WO | 2014001904 A1 | 1/2014 |
| WO | 2014004424 A1 | 1/2014 |
| WO | 2014009434 A1 | 1/2014 |
| WO | 2014018569 A1 | 1/2014 |
| WO | 2014018570 A1 | 1/2014 |
| WO | 2014018571 A2 | 1/2014 |
| WO | 2014018856 A1 | 1/2014 |
| WO | 2014018932 A2 | 1/2014 |
| WO | 2014031958 A1 | 2/2014 |
| WO | 2014041120 A1 | 3/2014 |
| WO | 2014052792 A1 | 4/2014 |
| WO | 2014056897 A1 | 4/2014 |
| WO | 2014066442 A2 | 5/2014 |
| WO | 2014074846 A1 | 5/2014 |
| WO | 2014076231 A1 | 5/2014 |
| WO | 2014076569 A2 | 5/2014 |
| WO | 2014081598 A1 | 5/2014 |
| WO | 2014086739 A1 | 6/2014 |
| WO | 2014093114 A1 | 6/2014 |
| WO | 2014104784 A1 | 7/2014 |
| WO | 2015179782 A1 | 11/2015 |
| WO | 2016018993 A1 | 2/2016 |

OTHER PUBLICATIONS

Abitec, CapmulPG8, CAS No. 31565-12-5, version 11, 2006, Columbus, OH.
Abitec, Excipients tbr the Pharmaceutical Industry—Regulatory and Product Information, 2013, 2 pages.
Acarturk, Fusun, Mucoadhesive Vaginal Dtug Delivery System, Recent Patents on Drug Delivery & Formulation, 2009, vol. 3, pp. 193-195.
Alabi, K. A., et al., Analysis of Fatty Acid Composition of Thevetia priuviana and Hura crepitans Seed oils using GC-FID, Fountain Journal of Nat. and Appl. Sciences, vol. 2(2), pp. 32-37, 2013, Osogbo.
Alexander, KS, Corn Oil, CAS No. 8001-30-7, Jan. 2009.
Alvarez et al., Ectopic uterine tissue as a chronic pairsgenerator, Neuroscience, Dec. 6, 2012, 225: 269-272.
Application Note FT-IR: JI-Ap-FT0508-008, CD spectra of pharmaceuticals substances—Steroids (2), JASCO International Co., Ltd., 2 pages.
Araya-Sibija et al., Crystallization of progesterone polymorphs using polymer-induced heteronucleation (PIHn) method, Drug Development and Industrial Pharmacy, Early Online, pp. 1-8, 2014, Informa Healthcare.
Araya-Sibija, Andrea M.A., Morphology Study of Progesterone Polymorphs Prepared by Polymer-Induced Heteronucleation (PIHn), Scanning vol. 35 pp. 213-221, 2013, Wiley Period., Inc.
Araya-Sibija, Andrea Manela, et al., Chemical Properties of Progesterone Selected Refer., SciFinder, 2014, American Chemical Society & US Natl. Lib. of Med.
Araya-Sibija, Andrea Manela, et al., Polymorphism in Progesterone Selected References, SciFinder, Feb. 24, 2014, pp. 1-12, American Chem. Society & Natl. Lib. of Med.
Araya-Sibija, Andrea Manela, et al., Polymorphism in Progesterone, SciFinder, pp. 1-46, Feb. 24, 2014, American Chem. Society & Natl. Lib. of Med.
Archer et al., Effects of ospemifene on the female reproductive and urinary tracts: translation from preclinical models into clinical evidence, Menopause: The Journal of the North American Menopause Society, vol. 22, No. 77, pp. 1-11 (2015).
Archer et al., Estrace® vs Premarin® for Treatment of Menopausal Symptoms: Dosage Comparison Study, Advances in Therapy®, vol. 9 No. 1, Jan./Feb. 1992.
Ashburn et al., Cardiovascular, Hepatic and Renal Lesions in Mice Receiving Cortisone, Estrone and Progesterone, Yale J Bilogy and Medicine, vol. 35, Feb. 1963, pp. 329-340.
Azeem, Adnan et al., Microemulsions as a Surrogate Carrier for Dermal Drug Delivery, Drug Development and Industrial Pharmacy, May 2000, vol. 35, No. 5, pp. 525-547 (abstract only). http://informahealthcare.com/doi/abs/10.1080/03639040802448646.
Azure Pharma, Inc., ELESTRIN™—Estradiol Gel, Deng Info, http://dailymed.nlm.nih.gov/dailymed/archives/fdaDrugInfo.cfm?archiveid=11885, 26 pages, Aug. 2009.
Bakhivritova-Albert, Ekaterina, et al., Enhancing Aqueous Dissolution Rates of Progesterone via Cocrystallization, SSCI, Division of Aptuit, Poster No. R6247, West Lafayette
Banerjee, Sila, et al., On the Stability of Salivary Progesterone Under Various Conditions of Storage, Steroids, vol. 46(6), pp. 967-974, Dec. 1985.
Barnett, Steven M, Pressure-tuning infrared and solution Raman spectroscopic studies of 17B-esiradiol and several A-ring . . . , Vibrational Spectroscopy 8, Elsevier, pp. 263, 1995.
Bartosova, Transdermal Drug Delivery In Vitro Using Diffusion Cells, Current Medicinal Chemistry, 2012, 19, 4671-4677, Bentham Science Publishers.
Benbow et al., Distribution and Metabolism of Maternal Progesterone in the Uterus, Placenta, and Fetus during Rat Pregnancy, Biology of Reproduction 52, 1327-1333 (1995).
Bernabei, M.T., et al., Release of progesterone polymorphs from dimethylpolysiloxarie polymeric matrixes, Bollettino Chimico Farmaceutico, vol. 122(1) pp. 20-26, 1983 SciFinder.
Bhavnani Bhagu R. et al., "Misconception and Concerns about Bioiciential Hormones Used for Custom-Compounded Hormone Therapy," J Clin Endocrinol Metab, Mar. 2012, 97(3):756-759.
Bhavnani et al., Structure Activity Relationships and Differential Interactions and Functional Activity of Various Equine Estrogens Mediated via Estrogen Receptors (ERs) ERα and ERβ, Endocrinology, Oct. 2008, 149(10):4857-4870.
Bhavnani, B.R., Stanczyk, F.Z., Pharmacology of conjugated equine estrogens: Efficacy, safety and mechanism of action, J. Steroid Biochem. Mol. Biol. (2013), Elsevier.
Bhavnani, B.R., Stanczyk, F.Z., Use of medroxyprogesterone acetate for hormone therapy in postmenopausal women: Is it safe? J. Steroid Biochem. Mol. Biol. (2013), Elsevier.
BioMed Central, Solubility of Progesterone in Organic Solvents, Online PDF, http://www.biomedcentral.com/content/supplementary/1475-2859-11-106-S2.pdf.
Blake et al., Single and multidose pharmacokinetic study of a vaginal micronized progesterone insert (Endometria) compared with vaginal gel in healthy reproductiveaged female subjects, Fertility and Sterility# vol. 94, No. 4, Sep. 2010, Elsevier.
Borka, Laszlo, Crystal Polymorphism of Pharmaceuticals, Acta Pharm, Jugosl., vol. 40 pp. 71-94, 1990.
Brinton, L.A., Felix, A.S., Menopausal hormone therapy and risk of endometrial cancer, J. Steroid Biochem Mol. Biol. (2013), Elsevier
British Pharmacocopoeia 2014 Online, Refined Maize Oil, Ph. Eur. Monograph 1342, vol. I & II, Monographs: Medicinal and Pharmaceutical Substances , http://www.pharmacopoeia.co.uk/bp2014/ixbin/bp.cgi?a=print&id-7460&tab=a-z%20index [Feb. 3, 2014 1:37:50 PM].
Burry, Kenneth A, Percutaneous absorption of progesterone in postmenopausal women treated with transdermal estrogen, Am J Obstet Gynecol, vol. 180(6) part 1, pp. 1504-1511, 1999.
Busetta, Par Bernard, Structure Cristalline et Moleculair de l'Oestradiol Hemihydrate, Acta Cryst., B28 pp. 560, 1972, Bis(dimethyl-o-thiolophenylarsine)palladium(II).
Busetta, Par Bernard, Structure Cristalline et Moleculaire du Complexe Oestradiol-Propanol, Acta Cryst., B28 pp. 1349, 1972, J.A. Kanters and J. Kroon.
Campsteyn, Par H, et al., Structure Cristalline et Molcculaire de la Progesterone C21H30O2, Acta Cryst., B28 pp. 3032-3042, 1972.

(56) References Cited

OTHER PUBLICATIONS

Cendejas-Saniana, G, et al., Growth and characterization of progesterone crystallites, Revista Mexicana de Fisica, 50, Suplemento 1 pp. 1-3, 2004.
ChemPro, Top-Notch Technology in Production of Oils and Fats, Chempro-Edible-Oil-Refining-ISO-TUV-Austria.
Christen et al., Phase I/Pharmacokinetic Study of High-Dose Progesterone and Doxorubicin, J Clin Oncol 11:2417-2426, 1993.
Christensson et al., Limonene hydroperoxide analogues differ in allergenic activity, Contact Dermatitis 2008: 59:344-352.
Christensson et al., Limonene hydroperoxide analogues show specific patch test reactions, Contact Dermatitis, 70, 291-299, 2014.
Christensson et al., Positive patch test reactions to oxidized limonene: exposure and relevance , Contact Dermatitis, 71, 264-272, 2014.
Chun et al., Transdermal Delivery of Estradiol and Norethrindrone Acetate: Effect of Vehicles . . . , J. Kor. Pharm. Sci., vol. 35 No. 3, pp. 173-177 (2005).
Cicinelli et al., Direct Transport of Progesterone From Vagina to Uterus, Obstetrics & Gynecology, vol. 95, No. 3, Mar. 2000, pp. 403-406.
Cole, Wayne & Julian, Percy L, Sterols. I. A Study of the 22-Ketosteroids, Cont. of the Research Lab. of the Glidden Co., Soya Prod. Div., vol. 67 pp. 1369-1375, Aug. 1945, Chicago.
Committee Opinion, Incidentally Detected Short Cervical Length, Committee of Obstetric Practice, Obstetrics & Gynecology, ACOG, vol. 119, No. 4, Apr. 2012, pp. 879-882.
Commodari, Fernando, Comparison of 17β-estradiol structures from x-ray diffraction and solution NMR, Magn. Resort. Chem., vol. 43, pp. 444-450, 2005, Wiley InterScience.
Cooper, A, et al., Systemic absorption of progesterone from Progest cream in postmenopausal women, The Lancet, vol. 351, pp. 1255-1256, Research Letters, Apr. 25, 1998
Corbett et al., "Trends in Pharmacy Compounding tor Women's Health in North Carolina: Focus on Vulvodynia," Southern Medical Journal, vol. 107, No. 7, Jul. 2014, pp. 433-436.
Corn Refiners Association, Corn Oil, 5th Edition, Washington, D.C., 2006.
Critchley et al., Estrogen Receptor β, But Not Estrogen Receptor α, Is Present in the Vascular Endothelium of the Human and Nonhuman Primate Endometrium, The Journal of Clinical Endocrinology Metabolism, 2001, vol. 86, No. 3, pp. 1370-1378.
Dauqan, Eqbil M. A., et al., Fatty Acids Composition of Four Different VegetableOils (Red Palm Olein, Palm Olein, Corn Oil, IPCBEE, vol. 14, 2011, IACSIT Press, Singapore.
Dideberg, O, et al., Crystal data on progesterone (C21H30O2), desoxycorticosterone (C21H30O3) corticosterone (C21H30O4) and aldosterone . . . , J. Appl. Cryst. vol. 4 pp. 80, 1971.
Diramio, Jackie A., Polyethylene Glycol Methacrylate1Dimetactylate Hydrogels for Controlled Release of Hydrophobic Drugs, Masters of Science Thesis, University of Georgia, Athens, Georgia, 2002, 131 pages.
Drakulic, Branko J, Role of complexes tbrmation between drugs and penetration enhancers in transdermal . . . , Inter. Journal of Pharmaceutics, Elsevier, vol. 363, pp. 40-49, 2009.
Du et al., Percutaneous progesterone delivery via cream or gel application in postmenopausal women: a randomized cross-over study of progesterone levels in serum, whole blood, saliva, and capillary blood, Menopause: The Journal of the North American Menopause Society, 2013, vol. 20, No. 11, pp. 1-7.
Duax, William L, et al., Conformation of Progesterone Side Chain: Conflict between X-ray Data and Force-Field Calculations, J. Am. Chem. Soc., vol. 103 pp. 6705-6712, Jun. 1981.
Duclos, R, et al., Polymorphism of Progesterone: Influence of the carrier and of the solid dispersion manufacturing . . . , J. Thermal Anal., vol. 37 pp. 1869-1875, 1991, Wiley.
Ebian, A.R., Ebian Article: Polymorphism and solvation of ethinyl estradiol, SciFinder, Pharmaceutica Acta Helvetiae, vol. 54(4), pp. 111-114, 1979, Alexandria, Egypt.

Eisenberger, A., Westhoff, C., Hormone replacement therapy and venous thromboembolism, J. Steroid , Biochem. Mol. Biol. (2013), Elsevier.
Engelhardt et al., Conceptus Influences the Distiibution of Uterine Leukocytes During Early Porcine Pregnancy, Biology of Reproduction 66, 1875-1880 (2002).
Estradiol, The Merck Index Online, Royal Society of Chemistry, https://www.rsc.org/Merck-Index/monograph/mono1500003758/estradiol?q=unauthorize.
Ettinger et al., Comparison of endometrial growth produced by unopposed conjugated estrogens or by micronized estradiol in postmenopausal women, Am J Obstet Gynecol 1997; 176:112-117
Excipients for Pharmaceuticals, Sasol Olefins & Surfactants GMBH, 2010, 28 pages.
Faassen, Fried, Physicochemical Properties and Transport of Steroids across Caco-2 Cells, Pharmaceutical Research, vol. 20(2), 2003, Plenum Pub. Corp.
FDA, Draft Guidance on Progesterone, Recommended Apr. 2010, Revised Feb. 2011 http://www.fda.gov/downloads/Drugs/GuidanceComplimceRegulatoryInformation/Guidances/UCM209294.pdf.
Ferrari, Roseli AP., et al., Oxidative Stability of Biodiesel From Soybean Oil Fatty Acid Ethyl Esters, Sci. Agric., vol. 62(3), pp. 291-295, 2005, PiracicaB1, Braz.
Filipsson et al., Concise International Chemical Assessment Document 5: Limonene, first draft, World Health Organization, Geneva, 1998, 36 pages.
Final Report on true Safety Assessment of BHT, International Journal of Toxicology, 21(Suppl. 2):19-94, 2002/.
Flyvholm, Sensitizing risk of butylated hydroxytoluene Blsed on exposure and effect data, Contact Dermatitis 1990: 23: 341-345.
Fotherby, K., Bioavailability of Orally Administered Sex Steroids Used in Oral Contraception and Hormone Replacement Therapy, Contraception, 1996; 54:59-69.
Franklin et al., Characterization of immunoglobulins and cytokines in human cervical mucus: influence of exogenous and endogenous hormones, Journal of Reproductive Immunology 42 (1999) 93-106, Elsevier.
Franz et al., Use of Excised Human Skin to Assess the Bioequivalence of Topical Products, Skin Pharmacol Physiol 2009;22:276-286.
Freedman, R.R., Menopausal hot flashes: Mechanisms, endocrinology, treatment, J. Steroid Biochem. Mol. Biol.(2013), Elsevier.
Fuchs et al., The Effects of an Estrogen and Glycolic Acid Cream on the Facial Skin of Postmenopausal Women: A Randomized Histologic Study, Cutis. Jun. 2003;71(6):481-8.
Fugh-Berman, Adriane, Bioidentical Hormones for Menopausal HormoneTherapy: Variation on a Theme, Journal of General Internal Medicine, vol. 22, pp. 1030-1034, 2007.
Furness et al., Hormone therapy in postmenopausal women and risk of endometrial hyperplasia (Review), 2012, pp. 1-204, The Cochrane Collaboration, Published by JohnWiley & Sons, Ltd.
Gäfvert et al., Free radicals in antigen formation: reduction of contact allergic response to hydroperoxides by epidermal treatment with antioxidants, British Journal of Dermatology 2002; 146: 649-656.
Ganam-Quintanar et al., Evaluation of the transepidermal permeation of diethylene glycol monoethyl ether and skin water loss, International Journal of Pharmaceutics, vo. 147, No. 2, Feb. 28, 1997, pp. 165-171 (abstract only).
Gattefossé SAS, Material Safety Data Sheet, Gelot 64, 2012, 8 pages.
Gattefossé SAS, Regulatory Data Sheet, Gelot 64, 2012, 6 pages.
Gattefossé SAS, Regulatory Data Sheet, Lauroglycol 90, 2012, 5 pages.
Gattefossé, "Excipients for Safe and Effective Topical Delivery, Drug Development and Delivery" Jul./Aug. 2012, http://drug-dev.com/Main/B1ck-Issues/Transdermal-Topical-Subciatanewis-Noninvasive-Deliv-5.aspx#.
Geelen, Math J.H. et al., "Dietary medium-chain fatty acids raise and (n-3) polyunsaturated fatty acids lower hepatic triacylglycerol synthesis in rats," The Journal of Nutrition, 1995, 125(10):2449-2456.

(56) References Cited

OTHER PUBLICATIONS

Gillet et al., Induction of amenorrhea during hormone replacement therapy: optimal micronized progesterone dose. A multicenter study, Maturitas 19 (1994) 103-115.
Giron-Forest, D, et al., Thermal analyis methods for pharmacopoeial materials, J. Pharmaceutical & Biomedical Anal., vol. 7(12) pp. 1421-1433, 1989, Pergamon Press, Gr. Britain.
Giron-Forest, D, Thermal analysis and calorimetric methods in the characterisation of polymorphs and solvates, Thermochimica Aces, vol. 248 pp. 1-59, 1995, Elsevier
Glaser et al, Pilot Study: Absorption and Efficacy of Multiple Hormones Delivered in a Single Cream Applied to the Mucous Membranes oldie Labia and Vagina, Gynecol Obstet Invest 2008;66:111-118
Golatowski et al., Comparative evaluation of saliva collection methods for proteome analysis, Clinica Chimica Acta 419 (2013) 42-46.
Graham et al, Physiological Action of Progesterone in Target Tissues, Endocrine Reviews, 1997, vol. 18, No. 4, pp. 502-519.
Groothuis et al., Estrogen and the endometrium: lessons learned from gene expression profiling in rodents and human, Human Reproduction Update, vol. 13, No. 4 pp. 405-417, 2007.
Gunstone, Frank D, et al., Vegetable Oils in Food Technology: Composition, Properties and Uses, Blackwell Publishing, CRC Press, 2002.
Gurney, E.P. et al., The Women's Health Initiative trial and related studies: 10 years later: A clinician's view, J.Steroid Biochem. Mol. Biol. (2013), Elsevier.
Hamid et al., The effects of common solubilizing agents on the intestinal membrane Blrrier functions and membrane toxicity in rats, International Journal of Pharmaceutics 379 (2009) 100-108, Elsevier.
Haner, Barbara, Crystal data (I) for some pregnenes and pregnadienes, Acta Cryst., vol. 17 pp. 1610, 1964.
Hapgood, J.P., et al., Potency of progestogens used in hormonal therapy: Toward understanding differential actions, J. Steroid Biochem. Mol. Biol. (2013), Elsevier.
Hargrove et al., Menopausal Hormone Replacement Therapy with Continuous Daily Oral Micronize Estradiol and Progesterone, Obstet Gynecol, vol. 73, No. 4, Apr. 1989, pp. 606-612.
Hatton et al., "Safety and efficacy of a lipid emulsion containing medium-chain triglycerides," Clinical Pharmacy, 1990, vol. 9, No. 5, pp. 366-371.
He et al., Apoptotic Signaling Pathways in Uteri of Rats with Endometrial Hyperplasia Induced by Ovariectomy Combined with Estrogen, Gynecol Obstet Invest 2013;76:51-56.
Helbling, Ignacio M, el. al., The Optimization of an Intravaginal Ring Releasing Progesterone Using a Mathematical Model, Pharm Res, vol. 31 pp. 795-808, 2014, Springer Science.
Helmy el. al., Estrogenic Effect of Soy Phyloestrogens on the Uterus of Ovariectomized Female Rats, Clinic Phwmacol Biopharmaceut, 2014, S2, 7 pages.
Henderson, V.W., Alzheimer's disease: Review of hormone therapy trials and implications for treatment and prevention after . . . , J. Steroid Biochem, Mol. Biol. (2013), Elsevier.
Henriksen, Thormod, et al., An ENDOR Sturdy of Radiation-Induced Molecular Damage to Progesterone, Jour. of Mag. Resonance, vol. 63, pp. 333-342, 1985, Acedemic Press, Inc.
Herman, Anna et al., "Essential oils and their constituents as skin penetration enhancer for transdermal drug delivery: a review," 2014 Royal Pharmaceutical Society, Journal of Pharmacy and Pharmacology, pp. 1-13.
Hodis, H.N., Mack, W.J., Hormone replacement therapy and the association with heart disease and overall mortality: Clinical . . . , J. Steroid Biochem. Mol. Biol. (2013), Elsevier.
Hospital, Michel, et al., X-ray Crystallography of Estrogens and Their Binding to Receptor Sites, Mol. Pharmacology, vol. 8 pp. 438-445, Acedemic Press, Inc., 1972.
Hostynek, JJ, Predictinga bsorptiono f fragrancec hemicalst hrough human skin, j. Soc.C osmeCt. hem.,4 6, 221-229(Jul./Aug. 1995).
Hulsmann, Stefan, Stability of Extruded 17B-Estradiol Solid Dispersions, Pharmaceutical Development and Tech., vol. 6(2) pp. 223-229, 2001, Marcel Dekker, Inc.
Hurn et al., Estrogen as a Neuroprotectant in Stroke, Journal of Cerebral Blood Flow and Metabolism 20:631-652, 2000, Lippincott Williams &. Wilkins, Inc., Philadelphia.
Hyder et al., Synthetic Estrogen 17α-Ethinyl Estradiol Induces Pattern of Uterine Gene Expression Similar to Endogenous Estrogen 17β-Estradiol, JPET 290(2):740-747, 1999.
Idder, Salima, et al., Physicochemical properties of Progesterone, SciFinder, pp. 1-26, Feb. 24, 2014, American Chem. Society & US Natl. Lib. of Med.
ISR, ISR (App. No. PCT/USI2/66406).
ISR, ISR (App. No. PCT/US13/023309).
ISR, ISR and written opinion for PCT/US/13/46442, dated Nov. 1, 2013.
ISR, ISR and written opinion for PCT/US/13/46443, dated Oct. 31, 2013.
ISR, ISR and written opinion for PCT/US/13/46444, dated Oct. 31, 2013.
ISR, ISR and written opinion for PCT/US/13/46445, dated Nov. 1, 2013.
Johanson, Gunnar, Toxicity Review of Ethylene Glycol Monomethyl Ether and its Acetate Ester, Critical Reviews in Toxicology, 2000, vol. 30, No. 3 , pp. 307-345 (abstract only). http://informahealthcare.com/doi/abs/10.1080/10408440091159220.
Johnson, William S, et al., Racemic Progesterone, Tetrahedron Letters No. 4, pp. 193-196, 1963, Pergamon Press Ltd., Great Britain.
Joshi et al., Detection and synthesis of a progestagen-dependent protein in human endometrium, J Reprod Fert (1980) 59, 273-285.
Kanno et al., The OECD Program to Validate the Rat Uterotrophic Bioassay to Screen Compounds for in Vivo Estrogenic Responses: Phase 1, Environmental Health Perspectives • vol. 109 | No. 8 | Aug. 2001, pp. 785-794.
Karlberg et al., Air oxidation of d-limonene (the citrus solvent) creates potent allergens, Contact Dermatitis, 1992: 26: 332-340.
Karlberg et al., Influence of an anti-oxidant on the formation of allergenic compounds during auto-oxication of d-limonene, Ann. Occup. Hyg., vol. 38, No. 2, pp. 199-207, 1994.
Kaunitz, Andrew M., Extended duration use of menopausal hormone therapy, Menopause: The Journal of the North American Menopause Society, 2014, vol. 21, No. 6, pp. 1-3.
Khalil, Sah, Stability and Dissolution Rates of Corticosteroids in Polyethylene Glycol Solid Dispersions, Drug Dev. & Indus. Pharm., vol. 10(5) pp. 771-787, 1984, Marcel Dekker.
Kharode et al., The Pairing of a Selective Estrogen Receptor Modulator, Blzedoxifene, with Conjugated Estrogens as a New Paradigm for the Treatment of Menopausal Symptoms and Osteoporosis Prevention, Endocrinology 149(12):6084-6091, 2008.
Kim et al., Safety Evaluation and Risk Assessment of d-Limonene, Journal of Toxicology and Environmental Health, Part B: Critical Reviews, 2013, 16:1, 17-38 http://dx.doi,org/10.1080/10937404.2013.769418.
Kincl et al., Increasing Oral Bioavailability of Progesterone by Formulation, Journal of Steroid Biochemistry, 1978, vol. 9, pp. 83-84.
Knuth et al., Hydrogel delivery systems for vaginal and oral applications: Formulation and biological considerations, Advanced Drug Delivery Reviews, vol. 11, No. 1-2, Jul.-Aug. 1993, pp. 137-167 (abstract only).
Koga et al., Enhancing mechanism of Labrasol on intestinal membrane permeability of the hydrophilic drug gentamicin sulfate, European Journal of Pharmaceutics and Biopharmaceutics 64 (2006) 82-91.
Komm et al., Blzedoxifene Acetate: A Selective Estrogen Receptor Modulator with improved Selectivity, Endocrinology 146(9):3999-4008, 2005.
Korkmaz, Filiz, Byophysical Studies of Progesterone-Model Membrane Interactions, Thesis, Grad. School of Nat. and App, Sci. of the Middle East Tech. University, Sep. 2003.

(56) References Cited

OTHER PUBLICATIONS

Kotiyan, P.N., Stability indicating HPTLC method for the estimation of estradiol, Journal of Pharmaceutical Biomedical Analysis, vol. 22 pp. 667-671, 2000, Elsevier.

Krzyminiewski, R, et al., FPR Study of the Stable Radical in a y-Irradiated Single Crystal of Progesterone, Jour. of Mag. Resonance, vol. 46 pp. 300-305, 1982, Acedemic Press.

Kubli-Garhas, C, et al., Ab initio calculations of the electronic structure of glucocorticoids, Jour. of Mol. Structure, Theochem, vol. 454 pp. 267-275, 1998, Elsevier.

Kubli-Garfias, Carlos, Ab initio study of the electronic structure of progesterone and related progestins, Jour. of Mol. Structure, Theochem vol. 425, pp. 171-179, 1998, Elsevier (abstract only).

Kuhnert-Brandstaetter and Grimm. Zur Unterscheidung von losungsmittelhaltigen pseudopolymorphen Kristallformen and polymorphen Modifikationen bei Steroidhormonen.II, Mikrochimica Acta, vol. 1, pp. 127-139, 1968.

Kuhnert-Brandstaetter and Junger and Kofler. Thermo-microscopic and spectrophotometric: Determination of steroid hormones, Microchemical Journal 9, pp. 105-133, 1965.

Kuhnert-Brandstaetter and Kofler. Zur mikroskopischen Identitaisprufung and zur Polymorphic Sexualhonuone, Mikrochimica Acta, vol. 6, pp. 847-853, 1959.

Kuhnert-Brandstaetter and Linder. Zur Hydratbildung bei Steroidhormonen, Sci. Pharm, vol. 41(2), pp. 109-116, 1973.

Kumasaka et al., Effects of Various Forms of Progestin on the the Estro gen-Primed, Ovariectomized Rat, Endocrine Endocrine Journal 1994, 41(2), 161-169.

Kuon et al., A Novel Optical Method to Assess Cervical Changes during Pregnancy and anti Use to Evaluate the Effects of Progestins on Term and Preterm Labor, Am J Obstet Gynecol. Jul. 2011 ; 205(1): 82.e15-82.e20.

Kuon et al., Actions of progestins for the inhibition of cervical ripening and uterine contractions to prevent preterm birth, FVV in Obgyn, 2012, 4 (2): 110-119.

Kuon et al., Pharmacological actions of progestins to inhibit cervical ripening and prevent delivery depend upon their properties, the route of administration and the vehicle, Am J Obstet Gynecol. May 2010 ; 202(5): 455.e1-455.e9.

Labrie, et al., Intravaginal prasterone (DHEA) provides local action without clinically significant changes in serum concentrations of estrogens or androgens, Journal of Steroid Biochemistry & Molecular Biology, vol. 138, pp. 359-367, 2013, Elsevier.

Lacey, J.V. Jr., The WHI ten year's later: An epidemiologist's view, J. Steroid Biochem. Mol. Biol. (2013), Elsevier.

Lahiani-Skibi, Malika, Solubility and Dissolution Rate of Progesterone-Cyclodextrin . . . , Drug Development and Industrial Pharmacy, Informa Healthcare vol. 32, pp. 1043-1058, 2006.

Lancaster, Robert W, et al., The Polymorphism of Progesterone: Stabilization of a 'Disappearing' Polymorph by . . . , Jour. of Pharm. Sci., vol. 96(12) pp. 3419-3431, 2007, Wiley-Liss.

Land, Laura M, The influence of water content of triglyceride oils on the solubility of steriods, Pharmaceutical Research, vol. 22(5) May 2005, Springer Science+Business Media.

Lauer et al., "Evaluation of the hairless rat as a model for in vivo percutaneous absorption," Journal of Pharmaceutical Sciences, vol. 86, No. 1, Jan. 1997, pp. 13-18.

Leonetti et al., Transdermal progesterone cream as an alternative progestin in hormone therapy, Alternative Therapies, Nov./Dec. 2005, vol. 11, No. 6, pp. 36-38.

Leonetti, Helene B, et al., Topical progesterone cream has an antipmoiiferative effect on estrogen-stimulated endometrium, Fertility and Sterility, vol. 79(1), Jan. 2003

Lewis, John G. et al., Caution on the use of saliva measurements to monitor absorption of progesterone from transdermal creams in postmenopausal women, Maturitas, The European Menopause Journal, vol. 41, pp. 1-6, 2002.

Li, Guo-Chian, Solid-state NMR analysis of steroidal conthrmation of 17a- and 17B-estradiol in the absence and presence of lipi . . . , Steroids, Elsevier, vol. 77, pp. 185-192, 2012

Lobo, R.A., Foreword, J. Steroid Biochem. Mol. Biol. (2014), Elsevier.

López-Belmonte, Conigendum to "Comparative uterine effects on ovariectomized rats after repeated treatment with different vaginal estrogen formulations" [Maturitas 72 (2012) 353-358], Maturitas 74 (2013) 393, Elsevier.

Lucy et al., Gonadotropin-releasing hormone at estrus: lutenizing hormone, estradiol, and progesterone during . . . Biol Reprod Sep. 1986;35(2):300-311 (abstract only).

Lvova, M. SH., et al., Thermal Analysis in the Quality Control and Standardization of Some Drugs, J Thermal Anal., vol. 40 pp. 405-411, 1993, Wiley.

Madishetti et al., Development of domperidone bilayered matrix type transdermal patches: physicochernical, in vitro and ex vivo characterization, DARU vol. 18, No. 3, 2010, pp. 221-229.

Magness, R.R., et al., Estrone, Estradiol-17β and Progesterone Concentrations in Uterine Lymph and Systematic Blood throughout the Porcine Estrone Estrous Cycle, Journal of Animal Science, vol. 57, pp. 449-455, ISU, 1983.

Manson, JoAnn E. et al., "Menopausal hormone therapy and health outcomes during the intervention and extended poststoping phases of the women's health initiative randomized trials," JAMA, Oct. 2, 2013, vol. 310, No. 13, pp. 1353-1368.

McGuffy, Irena, Softgel Technology as a Lipid-Blsed Delivery Tool for Bioavailability Enhancement, Catalent Pharma Solutions, Somerset, NJ, Mar. 2011.

Mesley, R.J., Clathrate Formation from Steroids,Chemistry and Industry, vol. 37 pp. 1594-1595. Sep. 1965.

Miao, Wenbin, et al., Chemical Properties of Progesterone, SciFinder, 2014, American Chemical Society & US Natl. Lib. of Med.

Miles et al., Pharmacokinetics and endometrial tissue levels of progesterone after administration bv'Intramuscular and vaginal routes: a comparative study, Fertility and Sterility, vol. 62, No. 3, Sep. 1994, pp. 485-490.

Miller et al., Safety and Feasibility of Topical Application of Limonene as a Massage Oil to the Breast, Journal of Cancer Therapy, 2012, 3, 749-754.

Mueck, A.O. et al., Genomic and non-genomic actions of progestogens in the breast, J. Steroid Biochem. Mol.Biol. (2013), Elsevier.

Muramatsu, Mitsuo, Thermodynamic Relationship between a- and B-Forms of Crystalline Progesterone, J. Pharmaceutical Sciences, vol. 68(2) pp. 175-78, 1979, Amer. Pharm. Assoc.

Ng, Jo-Han et al., Advances in biodiesel fuel for application in compression ignition engines, Clean Techn Environ Policy, vol. 12, pp. 459-493, 2010, Springer-Verlag.

Nicklas, Martina, Preparation and characterization of marine sponge collagen nanoparticles and employment for the trans . . . , Drug Devel. & Indust. Pharmacy,35(9) pp. 1035, 2009.

Nilsson et al., Analysis of Contact Allergenic Compounds in Oxidized d-Limonene, Chromatographia vol. 42, No. 3/4, Feb. 1996, pp. 199-205.

Notelovitz, Morris, et al., Initial 17-b-Estradiol Dose for Treating Vasomotor Symptoms, Obstetrics & Gynecology, vol. 95(5), pp. 726-731, part 1, May 2000, Elsevier.

NuGen, What is NuGen HP Hair Growth System.

NuGest900, NuGest 900™.

O'Leary, Peter, Salivary, but not serum or urinary levels of progesterone are elevated after topical application of progesterone cream to pre- and post-menopausal women, Clinical Endocrinology, vol. 53 pp. 615-620, Blackwell Science 2000.

Opinion on the Diethylene Glycol Momoethyl Ether (DEGEE), Scientific Committee on Consumer Products, Dec. 19, 2006, 27 pages.

Outterson, K., The Drug, Anality and Security Act—Mind the Gaps, n engl j med 370;2 nejm.org Jan. 9, 2014, pp. 97-99.

Palamakula et al., Preparation and In Vitro Characterization of Self-Nanoemulsified Drug Delivery Systems of Coenzyme Q10 Using Chiral Essential Oil Components, Pharmaceutical Technology October 2004, pp. 74-88.

Panay et al., The 2013 British Menopause Society & Women's Health Concern recommendations on hormone replacement therapy, Menopause International: The Integrated Journal of Postreproduc-

(56) References Cited

OTHER PUBLICATIONS tive Health, published online May 23, 2013, Sage Publications. http://min.sagepub.com/content/early/2013/05/23/1754045313489645. 1.
Panchangnula et al., Development and evaluation of an intracutaneous depot formulation of corticosteroids using Transcutol . . . , J Pharm Pharmacol, Sep. 1991;43(9):609-614 (abstract only).
Parasuraman et al., Blood sample collection in small laboratory animals, Journal of Pharmacology & Pharmacotherapeutics | Jul.-Dec. 2010 | vol. 1 | Issue 2, pp. 87-93.
Park, Jeong-Sook, Solvent efcts on physicochemical behavior of estradiols recrystalized for transdermal delivery, Arch Pharm Res, vol. 31(1), pp. 111-116, 2008.
Park, Jeong-Sook, Use of CP/MAS solid-state NMR for the characterization of solvate . . . , European Journal of Pharmaceutics and Biopharmaceutics., vol. 60, pp. 407-412, 2005.
Parrish, Damon A., A new estra-1,3,5(10)-triene-3,17b-diol solvate: estradiol-methanol-water, Crystal Structure Comm., Intn'l Union ofCrystallography, ISSN 0108-2701, 2003.
Patel et al., Transdermal Drug Delivery System: A Review, www.thepharmajournal.com, vol. 1, No. 4, 2012, pp. 78-87.
Payne, R.S., et al., Examples of success crystal structure prediction: polymorphs of primidone and progesterone, Intl. Jour. of Pharma., vol. 177 pp. 231-245, 1999, Elsevier.
PCCA, Apothograin, PCCA, May 2014, Houston, TX.
Persson, Linda C, et al., Physicochemical Properties of Progesterone Selecte, SciFinder, pp. 1-5, Feb 24, 2014, American Chem. Society & US Natl. Lib. of Med.
Pfaus et al,, Selective facilitation asexual solicitation in the female rat by a melanocortin receptor agonist, PNAS, Jul. 6, 2004, vol. 101, No. 27, pp. 10201-1020.
Pheasant, Richard, Polymorphism of 17-Ethinylestradiol, Schering Corporation, Bloomfield, NJ, May 1950.
Pickles, VR, Cutaneous reactions to injection of progesterone solutions into the skin, Br Med Journal, Aug. 16, 1952, pp. 373-374.
Pinkerton et al., What are the concerns about custom-compounded "bioidentical" hormone therapy? Menopause: The Journal of the North American Menopause Society, vol. 21, No. 12, 2014,pp. 1-3.
Pinkerton, J.V., Thomas, S., Use of SERMs for treatment in postmenopausal women, J. Steroid Biochern. Mol. Biol. (2014), Elsevier.
Pisegna, Gisia L, A High-pressuie Vibrational Spectroscopic Study of Polymorphism in Steroids . . . , Thesis, McGill University, Dept. of Chem, Nov. 1999, Natl. Lib. of Canada.
Portman, David et al., One-year treatment persistence with local estrogen therapy in postmenopausal women diagnosed as having vaginal atrophy, Menopause, vol. 22, No. 11, 2015, pp. 000/000 (8 pages).
Position Statement, Management of symptomatic vulvovaginal atrophy: 2013 position statement of the North American Menopause Society (NAMS), Menopause, vol. 20, No. 9, pp. 888-902.
Practice Bulletin No. 141, Management of Menopausal Symptoms, Obstetrics & Gynecology, ACOG, vol. 123, No. 1, Jan. 2014, pp. 202-216.
Prajapati, Metal N, et al., A comparative Evaluation of Mono-, Di- and Triglyceride of Medium Chain Fatty Acids by Lipid/Surfactant/Water, Springerlink.com, pp. 1-21, Apr. 2011.
Prausnitz et al., Transdermal drug delivery, Nat Biotechnol. Nov. 2008 ; 26(11): 1261-1268.
Price, Sarah L, The computational prediction of pharmaceutical crystal structures and polymorphism, Adv. Drug Delivery Reviews, vol. 56 pp. 301-319, 2004, Elsevier.
Product Information Sheet, Body BIlance Cream, Tahitian Noni International, 2013, 1 page.
Product Safety Assessment: Diethylenc Glycol Monoethyl Ether, Created: Sep. 24, 2007 The Dow Chemical Company Page, 5 pages.
Progesterone, The Merck index Online, Royal Society of Chemistry, 2013, search Feb. 17, 2014 https://www.rsc.org/Merck-Index/monograph/print/mono1500007889/progesterone?q=authorize.
Progynova TS 100, available online at file:///C:/Users/Call%20Family/Desktop/Progynova%20TS%20100%2012%20Patches_Pack%20%28Estradiol%20Hemihydrate%29.html, 2010.
Provider Data Sheet, About Dried Blood Spot Testing, ZRT Laboratory, 2014, 3 pages.
Rahn et al., Vaginal Estrogen for Genitourinary Syndrome of Menopause a Systematic Review, Obstet Gynecol 2014;124(6):1147-56.
Rao, Rajeswara et al., "Intra Subject Variability of Progesterone 200 mg Soft Capsules in Indian Healthy Adult Postmenopausal Female Subjects under Fasting Conditions," J Bioequiv Availab. 2014, 6: 139-143.
Reisman et al., Topical Application of the Synthetic Triterpenoid RTA 408 Protects Mice from Radiation-Induced Demiatis, Radiation Research 181, 512-520 (2014).
Rosilio, V, et al., Physical Aging of Progesterone-Loaded Poly(D,L,-lactide-co-glycolide) Microspheres, Phamiaceutical Research, vol. 15(5) pp. 794-799,1998, Plenum Pub. Corp.
Ross et al., Randomized, double-blind, dose-ranging study of the endometrial effects of a vaginal progesterone gel in estrogen-treated postmenopausal women, AnnJ Obstet Gynecol, Oct. 1997, vol, 177, No. 4, pp. 937-941.
Ruan et al., Systemic progesterone therapy—Oral, vaginal, injections and even transdermal? Maturitas 79 (2014) 248-255, Elsevier.
Salem, HF, Sustained-release progesterone nanosuspension following intramuscular injection in ovariectomized rats, International Journal of Nanomedicine 2010:5 943-954, Dove Press.
Salole, Eugene G., Estradiol, Analytical Profiles of Drug Substances, vol. 15, pp. 283-318, 1986.
Salole, Eugene G., The physicochemical properties of oestradiol, Journal of Pharmaceutical & Biomedical Analysis, vol. 5, No. 7, pp. 635-648, 1987.
Santen, R.J., Menopausal hormone therapy and breast cancer, J. Steroid Biochem. Mol. Biol. (2013), Elsevier.
Santen, RJ, Vaginal administration of estradiol: effects of dose, preparation and timing on plasma estradiol levels, CLIMACTERIC 2014;17:1-14
Sarkar, Bisu et al., Chemical Stability of Progesterone in Compounded Topical Preparations using PLO Transdermal Cream™ and HRT Cream™ B l se . . . , J Steroids Horm Sci, 4:2, 2013.
Sarrel, et al., The Mortality Toll of Estrogen Avoidance: An Analysis of Excess Deaths Among Hysterectornized Women Aged 50 to 59 Years, American Journal of Public Health, Research and Practice, e1-e6. Published online ahead of print Jul. 18, 2013.
Satyanarayana, D, et al., Aqueous Solubility Predictions of Aliphatic Alcohols, Alkyl Substituted Benzoates and Steroids, Asian J. Chem., vol. 9 (3) pp. 418-426, 1997.
Scavarelli, Rosa Maria, et al., Progesterone and Hydrate or Solvate, SciFinder, pp. 1-2, Feb. 24, 2014, American Chem. Society.
Schindler, A.E., The "newer" progestogens and postmenopausal hormone therapy (HRT) J. Steroid Biochem.Mol. Biol. (2013), Elsevier.
Schindler, Aldof E. et al., Classification and pharmacology of progestins, Maturitas 46S1 (2003) S7-S16.
Schutte et al., A tissue engineered human endometrial stroma that responds to cues for secretory differentiation, decidualization and menstruation, Fertil Steril. Apr. 2012 ; 97(4): 997-1003, Elsevier.
Schweikart et al., Comparative Uterotrophic Effects of Endoxifen and Tamoxifen in Ovariectomized Sprague-Dawley Rats, Toxicologic Pathology, 42: 1188-1196, 2014.
SciFinder Scholar Prednisone Chemical Properties, SciFinder, 2014, pp. 1-7, National Library of Medicine.
SciFinder Scholar Prednisone Physical Properties, SciFinder, 2014, pp. 1-10, Natioinal Library of Medicine.
SciFinder Scholar Progesterone Experimental Properties, SciFinder, pp. 1-9, Feb. 24, 2014, American Chem. Society.
Serantoni, Foresti, et al., 4-Prepen-3,20-diose (progesterone, form II), Crystal Structure Comm., vol. 4(1) pp. 189-192, 1975, CAPLUS DataBlse.
Shao et al., Review Open Access Direct effects of metforrnin in the endometrium: a hypothetical mechanism for the treatment of women with PCOS and endometrial carcinoma, Journal of Experimental & Clinical Cancer Research 2014, 33(1):41, 11 pages.

(56) References Cited

OTHER PUBLICATIONS

Sharma, H.C., et al., Physical Properties of Progesterone Selected Refer, SciFinder, pp. 1-5, Feb. 24, 2014, American Chem. Society & US Natl. Lib. of Med.

Shrier et al., "Mucosal Immunity of the Adolescent Female Genital Tract," Journal of Adolescent Health, 2003; 32:183-186.

Shufelt et al., Hormone therapy dose, formulation, route delivery, and risk of cardiovascular events in women: findings from the Women's Health Initiative Observational Study, Menopause: The Journal of the North American Menopause Society, vol. 21, No. 3, 2014, pp. 1-7, 2013.

Siew, Adeline, moderator, Bioavailability Enhancement with Lipid-Blsed Drug-Delivery Systems, Pharmaceutical , Technology, Aug. 2014, pp. 28, 30-31.

Sigma-Aldrich, Progesterone-Water Soluble: powder, BioReagent, suitable for cell culture), MSDS available online: http://www.sigmaaldrich.com/catalog/product/sigma/p7556.

Simon et al., Effective Treatment of Vaginal atrophy with an Ultra-low-dose estradiol vaginal tablet, Obstetrics & Gynocology, vol. 112, No. 5, Nov. 2008, pp. 1053-1060.

Simon, James A., What if the Women's Health Initiative had used transdermal estradiol and oral progesterone instead? Menopause: The Journal of the North American Menopause Society, 2014, vol. 21, No. 7, pp. 1-15.

Sitruk-Ware et al., Progestogens in hormonal replacement therapy: new molecules, risks, and benefits, Menopause: The Journal of the North American Menopause Society. vol. 9, No. 1, pp. 6-15, 2002.

Sitruk-Ware, Regine, "Pharmacological profile of progestins," Maturitas 47 (2004) 277-283.

Sitruk-Ware, Regine, Oral Micronized Progesterone—Bioavailability pharmacokinetics, pharmacological and therapeutic implications—A review, Contraception, Oct. 1987, vol. 36, No. 4, pp. 373-402.

Smith et al., Lower Risk of Cardiovascular Events in Postmenopausal Women Taking Oral Estradiol Compared with Oral Conjugated Equine Estrogens, JAMA Internal Medicine, Published online Sep. 30, 2013, E1-E7. jamainternalmedicine.com.

Smyth et al., Summary of Toxicological Data, a 2-Yr Study of Diethylene Glycol Monoethyl Ether in Rats, Fd Cosmet. Toxicol. vol. 2, pp. 641-642, 1964.

Stanczyk et al., Thereapuitcaily equivalent pharmacokinetic profile across three application sistes fbr AG200-15, a novel low-estrogen dose contraceptive patch, Contraception, 87 (2013) pp. 744-749.

Stanczyk, F.Z. et al., "Perctilaneous administration of progesterone: blood levels and endometrial protection," Menopause: The Journal of the North American Menopause Society, 2005, vol. 12, No. 2, pp. 232-237.

Stanczyk, F.Z. et al., Ethinyl estradiol and 17β-estradiol in combined oral contraceptives: pharmacokinetics, pharmacodynamics and risk assessment, Contraception 87 (Jun. 2013) vol. 87, No. 6, pp. 706-727.

Stanczyk, F.Z., "All progestins are not created equal," Steroids 68 (2003) 879-880.

Stanczyk, F.Z., "Treatment of postmenopausal women with topical progesterone creams and gels: are they effective?" Climacteric: 2014;17 (Suppl 2):8-11.

Stanczyk, F.Z., Bhavnani, B.R,, Current views of hormone therapy for the management and treatment of postmenopausal women, J. Steroid Biochem. Mol. Biol. (2014), Elsevier.

Stein, Emily A, et al., Progesterone Physical Properties, SciFinder, pp. 1-46, Feb. 24, 2014, American Chem. Society & US Natl. Lib. of Med.

Stephenson et al., "Transdermal progesterone: Effects on Menopausal symptoms and on throthbotic, anticoagulant, and inflammatory factors in postmenopausal women," Int J Pharmaceutical Compounding, vol. 12, No. 4, Jul./Aug. 2008, pp. 295-304.

Strickley, Robert T., Solubilizing excipients in oral and injectable formulations, Pharmaceutical Research Feb. 2004, vol. 21, Issue 2, pp. 201-230 (abstract only).

Storcchi, Antonino, Fatty Acid Composition, and Triglyceride Structure of Com Oil, Hydrogenated Corn Oil, and Corn Oil Margarine, Journal of Food Science, vol. 47, pp. 36-39, 1981.

Struhar, M, et al., Estradiol Benzoate: Preparation of an injection suspension . . . , SciFinder, Cesko-Slovenska Farmacie, vol. 27(6), pp. 245-249, 1978, Bratislava, Czech.

Sullivan et al., "A review of the nonclinical safety of Transcutol®, a highly purified form of diethylene glycol monoethyl ether (DEGEE) used as a pharmaceutical excipient," Food and Chemical Toxicology, 72 (2014) pp. 40-50.

Sun, Jidong, D-Limonene: Safety and Clinical Applications, Alternative Medicine Review vol. 12, No. 3, 2007, pp. 259-264.

Tait, Alex D, Characterization of the Prod. from the Oxidation of Progesterone with Osmium Tetroxide, Dept of Investigative Med., Univ. Cambridge, Gt. Britain pp. 531-542, 1972.

Takacs M. et al., The light sensitivity of corticosteroids in crystalline form, Pharmaceutica acta Helvetiae, vol. 66 (5-6) pp. 137-140, 1991, Hardin Library.

Tan, Melvin S, et al., A Sensitive Method fbr the Determination of Progesterone in Human Plasma by LC-MS-MS, M1025, Cedra Corporation, Austin, Texas.

Tang et al., Effect of Estrogen and Progesterone on the Development of Endometrial Hyperplasia in the Fischer Biology of Rat, Biology of Reproduction 31, 399-413 (1984)

Tas et al., Comparison of antiproliferative effects of metformine and progesterone on estrogen-induced endometrial hyperplasia in rats, Gynecol Endocrinol, Early Online: 1-4, 2013, http://informahealthcare.com/gye.

Tella, S.H., Gallagher, J.C., Prevention and treatment of postmenopausal osteoporosis, J. Steroid Biochem. Mol. Biol. (2013), Elsevier Thomas, Joshua, et al., The effect of water solubility of solutes on their flux through human skin in vitro: An . . . , Intl. J. of Pharmaceut., vol. 339 pp. 157-167, 2007, Elsevier.

Thomas, Peter, Characteristics of membrane progestin receptor alpha (mPRα) and progesterone membrane receptor component 1 (PGMRC1) and their roles in mediating rapid progestin actions, Frontiers in Neuroendocrinology 29 (2008) 292-312.

Tripathi, R, et al., Study of Polymorphs of Progesterone by Novel Melt Sonocrysiallization Technique: A Technical Note, AAPS PhamSciTech, vol. 11, No. 3, Sep. 2010.

Trommer et al., Overcoming the stratum Corneum: The modulation of Skin Penetration, Skin Pharmacol Physlol 2006;19:106-121.

Tuleu et al., "Comparative Bioavailability Study in Dogs of a Self-Emulsifying Formulation of Progesterone Presented in a Pellet and Liquid Form Compared with an Aqueous Suspension of Progesterone," Journal of Pharmaceutical Sciences, vol. 93, No. 6, Jun. 2004, pp. 1495-1502.

Ueda et al., Topical and Transdermal Drug Products, Pharmacopeial Forum, vol. 35(3) [May-Jun. 2009], 750-754.

USP, 401 Fats and Fixed Oils, Chemical Tests,Second Suplement to USP36-NF31, pp. 6141-6151, 2013.

USP, Certificate—Corn Oil, Lot G0L404 Jul. 2013.

USP, Lauroyl Pohyoxylglycerides, Safety Data Sheet. US, 5611 Version 502, pp. 1-9, 2013.

USP, Monographs: Progesterone, USP29, www.pharmacopeia.cn/v29240/usp29nf24s0_m69870.html, search done: Feb 25, 2014.

USP, Official Monographs, Corn Oil, NF 31, pp. 1970-1971, Dec. 2013.

USP, Official Monographs, Lauraoyl Polyoxylglycerides, NF 31, pp. 2064-2066, Dec. 2013.

USP, Official Monographs, Medium Chain Triglycerides, NF 31, pp. 2271-2272, Dec. 2013.

USP, Official Monographs, Mono- and Di-glycerides, NF 31, pp. 2101, Dec. 2013.

USPTO_U.S. Appl. No. 12/561,515_Jan. 29, 2013_Advisory_Action.

USPTO_U.S. Appl. No. 12/561,515_Final Office Action dated Oct. 26, 2012 in U.S. Appl. No. 12/561,515.

USPTO_U.S. Appl. No. 12/561,515_Notice of Allowance dated Sep. 11, 2013 in U.S. Appl. No. 12/561,515.

USPTO_U.S. Appl. No. 12/561,515_Office Action dated Dec. 12, 2011 in U.S. Appl. No. 12/561,515.

(56) References Cited

OTHER PUBLICATIONS

USPTO_U.S. Appl. No. 13/684,002_Mar. 20, 2013_Non-Final_Office_Action.
USPTO_U.S. Appl. No. 13/684,002_Jul. 16, 2013_Final_Office_Action.
USPTO_U.S. Appl. No. 13/684,002_Dec. 6, 2013_Notice_of_Allowance.
USPTO_U.S. Appl. No. 13/843,362_Mar. 16, 2015_Restriction_Requirement.
USPTO_U.S. Appl. No. 13/843,428_Apr. 14, 2015_Restriction_Requirement.
USPTO_U.S. Appl. No. 14/099,545_Feb. 18, 2014_Non-Final_Office_Action.
USPTO_U.S. Appl. No. 14/099,545_Jul. 14, 2014_Notice_of_Allowance.
USPTO_U.S. Appl. No. 14/099,562_Feb. 20, 2014_Restriction_Requirement.
USPTO_U.S. Appl. No. 14/099,562_Mar. 27, 2014_Non-Final_Office_Action.
USPTO_U.S. Appl. No. 14/099,562_Jul. 2, 2014_Final_Office_Action.
USPTO_U.S. Appl. No. 14/099,562_Dec. 10, 2014_Notice_of_Allowance.
USPTO_U.S. Appl. No. 14/099,571_Mar. 28, 2014_Restriction_Requirement.
USPTO_U.S. Appl. No. 14/099,571_Jul. 15, 2014_Notice_of_Allowance.
USPTO_U.S. Appl. No. 14/099,582_Apr. 29, 2014_Restriction_Requirement.
USPTO_U.S. Appl. No. 14/099,582_Jun. 17, 2014_Non-Final_Office_Action.
USPTO_U.S. Appl. No. 14/099,582_Nov. 7, 2014_Notice_of_Allowance.
USPTO_U.S. Appl. No. 14/099,582_Jan. 22, 2015_Notice_of_Allowance.
USPTO_U.S. Appl. No. 14/099,598_May 13, 2014_Restriction_Requirement.
USPTO_U.S. Appl. No. 14/099,598_Jul. 3, 2014_Non-Final_Office_Action.
USPTO_U.S. Appl. No. 14/099,598_Dec. 10, 2014_Notice_of_Allowance.
USPTO_U.S. Appl. No. 14/099,612_Mar. 20, 2014_Restriction_Requirement.
USPTO_U.S. Appl. No. 14/099,612_Oct. 30, 2014_Non-Final_Office_Action.
USPTO_U.S. Appl. No. 14/099,612_Nov. 26, 2014_Notice_of_Allowance.
USPTO_U.S. Appl. No. 14/099,623_Mar. 5, 2014_Restriction_Requirement.
USPTO_U.S. Appl. No. 14/099,623_Jul. 18, 2014_Non-Final_Office_Action.
USPTO_U.S. Appl. No. 14/099,623_Dec. 15, 2014_Notice_of_Allowance.
USPTO_U.S. Appl. No. 14/103,355_Dec. 8, 2014_Non-Final_Office_Action.
USPTO_U.S. Appl. No. 14/106,655_Jul. 3, 2014_Restriction_Requirement.
USPTO_U.S. Appl. No. 14/125,554_Dec. 5, 2014_Restriction_Requirement.
USPTO_U.S. Appl. No. 14/125,554_Apr. 14, 2015_Non-Final_Office_Action.
USPTO_U.S. Appl. No. 14/136,048_Nov. 4, 2014_Restriction_Requirement.
USPTO_U.S. Appl. No. 14/136,048_Mar. 12, 2015_Non-Final_Office_Action.
USPTO_U.S. Appl. No. 14/475,814_Oct. 1, 2014_Non-Final_Office_Action.
USPTO_U.S. Appl. No. 14/475,814_Feb. 13, 2015_Notice_of_Allowance.
USPTO_U.S. Appl. No. 14/475,864_Feb. 11, 2014_Notice_of_Allowance.
USPTO_U.S. Appl. No. 14/475,864_Oct. 2, 2014_Non-Final_Office_Action.
USPTO_U.S. Appl. No. 14/476,040_Mar. 26, 2015_Restriction_Requirement.
USPTO_U.S. Appl. No. 14/521,230_Dec. 5, 2014__Restriction_Requirement.
USPTO_U.S. Appl. No. 14/521,230_Feb. 18, 2015_Non-Final_Office_Action.
USPTO_U.S. Appl. No. 14/624,051_Apr. 7, 2015_Non-Final_Office_Action.
Utian, Wulf H, et al., Relief of vasomotor symptoms and vaginal atrophy with lower doses of conjugated equine estrogens, Fertility and Sterility, vol. 75(6) pp. 1065, Jun. 2001.
Voegtline et al., Dispatches from the interface of salivary bioscience and neonatal research, Frontiers in Endocrinology, Mar. 2014, vol. 5, article 25, 8 pages.
Waddell et al., Distribution and metabolism of topically applied progesterone in a rat model, Journal of Steroid Biochemistry & Molecular Biology 80 (2002) 449-455.
Waddell et al., The Metabolic Clearance of Progesterone the Pregnant Rat: Absence of a Physiological Role for the Lung, Biology of Reproduction 40, 1188-1193 (1989).
Walter et al., The role of progesterone in endometrial angiogenesis in pregnant and ovariectomised mice, Reproduction (2005) 129 765-777.
Weber, E.J., Corn Lipids, Cereal Chem., vol. 55(5), pp. 572-584, The American Assoc of Cereal Chem, Sep.-Oct. 1978.
Weber, M.T., et al., Cognition and mood in perimenopause: A systematic review meta-analysis, J. Steroid Biochem. Mol. Biol. (2013), Elsevier.
Weintraub, Arlene, "Women fooled by untested hormones from compounding pharmacies," Forbes, Feb. 20, 2015; retrieved online at htt://onforb.es/1LIUm1V on Feb. 23, 2015, 3 pages.
Whitehead et al., Absorption and metabolism of oral progesterone, The British Medical Journal, vol. 280, No. 6217 (Mar. 22, 1980), pp. 825-827, BMJ Publishing Group.
Wiranidchapong, Chutima, Method of preparation does not affect the miscibility between steroid hormone and polymethacrylate, Thermochimica Acta 485, Elsevier, pp. 57, 2009.
Wood et al., Effects of estradiol with micronized progesterone or medroxyprogesterone acetate on risk markers for breast cancer in postmenopausal monkeys, Breast Cancer Res Treat (2007) 101:125-134.
Wren et al., Effect of sequential transdermal progesterone cream on endometrium, bleeding pattern, and plasma progesterone and salivary progesterone levels in postmenopausal women, Climacteric, 2000, 3(3), pp. 155-160. http://dx.doi.org/10.1080/13697130008500109.
Wu et al., Gene Expression Profiling of the Effects of Castration and Estrogen Treatment in the Rat Uterus, Biology of Reproduction 69, 1308-1317 (2003).
Yalkowsky, Samuel H, & Valvani, Shri C, Solubility and Partitioning 1: Solubility of Nonelectrolytes in Water, J. of Pharmaceutical Sciences, vol. 69(8) pp. 912-922, 1980.
Yalkowsky, Samuel H, Handbook of Acqueous Solubility Data, Solutions, pp. 1110-1111, CRC Press, Boca. Raton, London, New York, Wash. D.C.
Yue, W., Genotoxic metabolites of estradiol in breast: potential mechanism of estradiol induced carcinogenesis, Journal of Steroid Biochem & Mol Biology, vol. 86 pp. 477-486, 2003.
Zava, David T. et al., Percutaneous absorption of progesterone, Maturitas 77 (2014) 91-92, Elsevier.
Zava, David T., Topical Progesterone Delivery and Levels in Serum, Saliva, Capillary Blood, and Tissues, Script, ZRT Laboratory, pp. 4-5. http://www.zrtlab.com/component/docman/cat_view/10-publications?Itemid.
Castelo-Branco Camil et al., "Treatment of atrophic vaginitis," Therapy, 2007, vol. 4, No. 3, pp. 349-353.
Chambin et al., Interest of Multifunctional Lipid Excipients: Case of Gelucire® 44/14, Drug Development and Industrial Pharmacy, vol. 31, No. 6, pp. 527-534 (Year: 2005).

(56) References Cited

OTHER PUBLICATIONS

Cho, Y.A. et al., Transdermal Delivery of Ketorolac Tromethamine: Effects of Vehicles and Penetration Enhancers, Drug Development and Industrial Pharmacy, 30(6):557-564, Jun. 2004.
Cicinelli et al., "First uterine pass effect" is observed when estradiol is placed in the upper but not lower third of the vagina, Fertility and Sterility, vol. 81, No. 5, May 2004, pp. 1414-1416.
Cicinelli, Intravaginal oestrogen and progestin administration: advantages and disadvantages, Best Practices & Research Clinical Obstretrics and Gynaecology vol. 22, No. 2, 2008, pp. 391-405.
Crandall, Carolyn, "Vaginal Estrogen Preparations: A Review of Safety and Efficacy for Vaginal Atrophy," Journal of Women's Health, 2002, vol. 11, No. 10, pp. 857-877.
Cremer Care, "MIGLYOL® 810, 812 INCI: Caprylic/Capric Triglyceride," Cremer Oleo GmbH & Co. KG, pp. 1-7, available at. http://s3.amazonaws.com/petercremerna/products/spec_sheets/159/339/301/original/M IGL YOL_81 0_812_ TDS.pdf?1389204 445 (Mar. 2013) accessed on Dec. 30, 2016.
Garad S. et al., "Preclinical Development for Suspensions," A.K. Kulshreshtha el al. (eds.), Pharmaceutical Suspensions: From Formulation Development to Manufacturing, Springer, New York 2010, pp. 127-176.
Holm et al., "Examination of oral absorption and lymphatic transport of halofantrine in a triple-cannulated canine model after administration in self-microemulsifying drug delivery systems (SMEDDS) containing structured triglycerides," European Journal of Pharmaceutical Sciences 20 (2003) 91-97.
Humberstone, Andrew et al., "Lipid-based vehicles for the oral delivery of poorly water soluble drugs," Advanced Drug Delivery Reviews, 25 (1997) 103-128.
Karande, et al., Enhancement of transdermal drug delivery via synergistic action of chemicals, Biochimica et Bicphysica Acta, 1788:2362-2373, Sep. 2009.
Knuth et al., Hydrogel delivery systems for vaginal and oral applications: Formulation and biological considerations, Advanced Drug Delivery Reviews, vol. 11, No. 1-2, Jul.-Aug. 1993, pp. 137-167.
Lane, Majella E., "Skin penetration enhancers," International Journal of Pharmaceutics 447 (2013) 12-21.
Lindmark, Tuulikki et al., "Absorption Entrancement through Intracellular Regulation of Tight Junction Permeability by Medium Chain Fatty Acids in Carro-2 Cells," JPET 284(1):362-369, 1998.
Lindmark, Tuulikki et al., "Mechanisms of Absorption Enhancement by Medium Chain Fatty Acids in Intestinal Epithelial Caco-2 Cell Monolayers," JPET 275(2):958-964, 1995.
Lopes, Luciana B. et al., Enhancement of transdermal delivery of progesterone using medium-chain mono and diglycerides as skin penetration enhancers, Pharmaceutical Development and Technology, 14:5, 524-529, Mar. 2009.
Monti, D. et al., Effect of different terpene-containing essential oils on permeation of estradiol through hairless mouse skin, International Journal of Pharmaceutics, 237:209-24, 2002.
Pachman et al., "Management of menopause-associated vasomotor symptoms: Current treatment options, challenges and future directions," International Journal of Women's Health, May 7, 2010.
Potluri, Praveen and Guru V. Belageri, "Mixed-micellar proliposomal systems for enhanced oral delivery of progesterone," Drug Delivery, 2006, vol. 13, No. 3, pp. 227-232.
Prajapati Hetal N. et al., "A Comparative Evaluation of Mono-, Di- and Triglyceride of Medium Chain Fatty Acids by Lipid/Surfactant/Water Phase Diagram, Solubility Determination and Dispersion Testing for Application in Pharmaceutical Dosage Form Development," Pharm Res. Jan. 2012; 29(1): 285-305. Published online Aug. 23, 2011. doi: 10.1007/s11095-011-0541-3.
Prajapati Hetal N. et al., "Effect of Difference in Fatty Acid Chain Lengths of Medium-Chain Lipids on Lipid/Surfactant/Water Phase Diagrams and Drug Solubility," J. Excipients and Food Chem. 2 (3) 2011:73-88.
Rao, R. et al., "The Affect of Capmul, Labrafil and Transcutol on Progesterone 100 Mg Soft Capsules Bioavailability in Indian Healthy Adult Postmenopausal Female Subjects Under Fasting Conditions," Bioequivalence & Bioavailability, 7(2):095-107, 2015.
Sallee, Verney L. et al., "Determinants of intestinal mucosal uptake of short- and medium-chain fatty acids and alcohols," Journal of Lipid Research, 1973, vol. 14, 475-484.
Sarpal, K. et al., "Self emulsifying drug delivery systems: a strategy to improve oral bioavailability," Current Research & Information on Pharmaceuticals Sciences (CRIPS), 2010, vol. 11, No. 3, pp. 42-49.
Search Report, Extended European Search Report for EP13741053.6, dated Jul. 1, 2015.
Search Report, Extended European Search Report for EP13807188.1, dated Nov. 23, 2015.
Search Report, International Search Report and Written Opinion for PCT/US14/61811, dated Jan. 21, 2015.
Search Report, International Search Report and Written Opinion for PCT/US15/23041, dated Jun. 30, 2015.
Search Report, International Search Report and Written Opinion for PCT/US15/42621, dated Oct. 29, 2015.
U.S. Appl. No. 12/561,515 Dec. 12, 2011 Non-Final Office Action.
U.S. Appl. No. 12/561,515 Oct. 26, 2012 Final Office Action.
U.S. Appl. No. 12/561,515 Sep. 11, 2013 Notice of Allowance
U.S. Appl. No. 13/843,428 Jul. 2, 2015 Non-Final Office Action.
U.S. Appl. No. 14/106,655 Jun. 19, 2015 Final Office Action.
U.S. Appl. No. 14/690,955 Feb. 1, 2016 Non-Final Office Action.
Ettinger et al., "Measuring symptom relief in studies of vaginal and vulvar atrophy: the most bothersome symptom approach," Menopause, vol. 15, No. 5, 2008, pp. 885-889.
Eugster-Hausmann et al., "Minimized estradiol absorption with ultra-low-dose 10 µg 17β-estradiol vaginal tablets," Climacteric 2010;13:219-227.
Martelli, Mary Elizabeth, "Vaginal Medicine Administration," The Gale Encyclopedia of Nursing and Allied Health, Gale Group, 2002, pp. 2542-2543.
Regidor, P., "Progesterone in Peri- and Postmenopause: A Review," Geburtshilfe Frauenheilkd, Nov. 2014 74(11):995-1002.
Simon, James A. et al., "A vaginal estradiol softgel capsule, TX-004HR, has negligible to verylow systemic absorption of estradiol: Efficacy arid pharrnacokineticdata review," Maturitas 99 (2017) 51-58.
Stefanick, "Estrogens and progestins: background and history, trends in use, and guidelines and regimens approved by the US Food and Drug Administration," The American Journal of Medicine (2005) vol. 118 (126), 64S-73S.
Hitchcock, C. L. et al., "Oral micronized progesterone for vasomotor symptoms—a placebo-controlled randomized trial in healthy postmenopausal women," *Menopause: The Journal of the North American Menopause Society*, 19(8):886-893, The North American Menopause Society, United States (Aug. 2012).
Hosmer, J. et al., "Microemulsions Containing Medium-Chain Glycerides as Transdermal Delivery Systems for Hydrophilic and Hydrophobic Drugs," *AAPS PharmSciTech*, 10(2): 589-596, American Association of Pharmaceutical Scientists, United States (2009).
March, C. M. et al., "Roles of Estradiol and Progesterone in Eliciting the Midcycle Luteinizing Hormone and Follicle-Stimulating Hormone Surges," *The Journal of Clinical Endocrinology & Metabolism*, 49(4):507-513, The Endocrine Society, United States (Oct. 1, 1979).
Sofi, S. H., et al., "Gelucire: A Versatile Formulation Excipient," Ijppr.Human, 10(3): 55-73 (2017).
Tang, O.S., et al., "Pharmacokinetics of different routes of administration of misoprostol," Human Reproduction, 17(2):332-226, European Society if Human Reproduction and Embryology, Belgium (2002).
Wang, H., et al., "Pharmacokinetics of hard micronized progesterone capsules via vaginal or oral route compared with soft micronized capsules in healthy postmenopausal women: a randomized open-label clinical study," *Drug Des Devel Ther.*, 13:2475-2482, Dove Press, England (2019).
Co-pending Application, U.S. Appl. No. 16/833,213, Inventor, Bernick, B.A., filed Mar. 27, 2020 (Not Published).
Co-pending Application, U.S. Appl. No. 16/837,933, Inventor, Bernick, B.A., filed Apr. 1, 2020 (Not Published).

(56) References Cited

OTHER PUBLICATIONS

Co-pending Application, U.S. Appl. No. 16/837,937, Inventor, Bernick, B.A., filed Apr. 1, 2020 (Not Published).
Co-pending Application, U.S. Appl. No. 16/834,780, Inventor, Bernick, B.A., filed Mar. 30, 2020 (Not Published).
Co-pending Application, U.S. Appl. No. 16/834,844, Inventor, Bernick, B.A., filed Mar. 30, 2020 (Not Published).
Co-pending Application, U.S. Appl. No. 16/833,186, Inventor, Bernick, B.A., filed Mar. 27, 2020 (Not Published).
Co-pending Application, U.S. Appl. No. 16/833,188, Inventor, Bernick, B.A., filed Mar. 27, 2020 (Not Published).
Office Action dated Jan. 30, 2017, in U.S. Appl. No. 14/649,818 Inventors, Bernick, B.A., filed Jun. 4, 2015, 12 pages.
Office Action dated Nov. 2, 2017, in U.S. Appl. No. 14/649,818 Inventors, Bernick, B.A., filed Jun. 4, 2015, 21 pages.
Office Action dated Jun. 15, 2018, in U.S. Appl. No. 14/649,818 Inventors, Bernick, B.A., filed Jun. 4, 2015, 21 pages.
Office Action dated Jun. 3, 2017, in U.S. Appl. No. 14/649,818 Inventors, Bernick, B.A., filed Jun. 4, 2015, 15 pages.
Office Action dated Jan. 5, 2016, in U.S. Appl. No. 14/521,002 Inventors, Bernick, B.A., filed Oct. 22, 2014, 9 pages.
Office Action dated Jan. 6, 2017, in U.S. Appl. No. 14/521,002 Inventors, Bernick, B.A., filed Oct. 22, 2014, 10 pages.
Office Action dated Oct. 5, 2017, in U.S. Appl. No. 14/521,002 Inventors, Bernick, B.A., filed Oct. 22, 2014, 13 pages.
Office Action dated Jul. 20, 2018, in U.S. Appl. No. 14/521,002 Inventors, Bernick, B.A., filed Oct. 22, 2014, 16 pages.
Office Action dated Jun. 3, 2019, in U.S. Appl. No. 14/521,002 Inventors, Bernick, B.A., filed Oct. 22, 2014, 12 pages.
Office Action dated Apr. 2, 2020, in U.S. Appl. No. 14/521,002 Inventors, Bernick, B.A., filed Oct. 22, 2014, 6 pages.
Kingsburg, S.A. et al., "Treating dyspareunia caused by vaginal atrophy: a review of treatment options using vaginal estrogen therapy," *International Journal of Women's Health* 1:105-111, Dove Press, England (2009).
ACTIVELLA® (estradiol/ norethindrone acetate) prescribing information (Nov. 2017) FDA Label, 39 pages.
PROMETRIUM® (progesterone, USP) prescribing information (Jun. 2009) FDA Label, 33 pages.
VAGIFEM® (estradiol vaginal tablets) prescribing information (Nov. 2009) FDA Label, 14 pages.
Macbride, M.B., et al., "Vulvovaginal Atrophy," *Mayo Clinic Proceedings,* 85(1): 87-94, Elsevier, Netherlands (2010).
De Vries, T.P.G.M., et al, "Guide to Good Prescribing: A Practical Manual," Essential Medicines and Health Products Information Portal, World Health Organization, Annex 3 ("How to explain the use of some dosage forms"), Checklist 11 ("Vaginal tablet without applicator") available at https://apps.who.int/iris/handle/10665/59001 (4 pages)(1994).
Rioux, J.E., et al "17 beta-Estradiol Vaginal Tablet Versus Conjugated Equine Estrogen Vaginal Cream to Relieve Menopausal Atrophic Vaginitis," *Menopause,* 7(3): 156-161, The North American Menopause Society, United States (2000).

Cicinelli, E. et al. "Placement of the vaginal 17 beta-estradiol tablets in the inner or outer one third of the vagina affects the preferential delivery of 17 beta-estradiol toward the uterus or periurethral areas, thereby modifying efficacy and endometrial safety," *Am. J. Obstet. Gynecol.,* 189: 55-58 (2003).
Office Action dated Apr. 8, 2021, in U.S. Appl. No. 16/677,831, Bernick, B. A., et al., filed Nov. 8, 2019, 19 pages.
Office Action dated Apr. 7, 2021, in U.S. Appl. No. 16/746,434, Bernick, B. A., et al., filed Jan. 17, 2020, 14 pages.
Office Action dated Apr. 8, 2021, in U.S. Appl. No. 16/833,188, Bernick, B. A., et al., filed Mar. 27, 2020, 16 pages.
Office Action dated Aug. 7, 2020, in U.S. Appl. No. 16/833,213, Bernick, B. A., et al., filed Mar. 27, 2020, 14 pages.
Notice of Allowance dated Oct. 7, 2020, in U.S. Appl. No. 16/833,213, Bernick, B. A., et al., filed Mar. 27, 2020, 5 pages.
Office Action dated Jun. 25, 2020, in U.S. Appl. No. 16/834,844, Bernick, B. A., et al., filed Mar. 30, 2020, 12 pages.
Notice of Allowance dated Aug. 21, 2020, in U.S. Appl. No. 16/834,844, Bernick, B. A., et al., filed Mar. 30, 2020, 6 pages.
Office Action dated Oct. 6, 2020, in U.S. Appl. No. 16/837,933, Bernick, B. A., et al., filed Apr. 1, 2020, 14 pages.
Final Office Action dated Feb. 4, 2021, in U.S. Appl. No. 16/837,933, Bernick, B. A., et al., filed Apr. 1, 2020, 15 pages.
Notice of Allowance dated Mar. 12, 2021, in U.S. Appl. No. 16/837,933, Bernick, B. A., et al., filed Apr. 1, 2020, 7 pages.
Office Action dated Jul. 10, 2020, in U.S. Appl. No. 16/837,937, Bernick, B. A., et al., filed Apr. 1, 2020, 14 pages.
Final Office Action dated Nov. 30, 2020, in U.S. Appl. No. 16/837,937, Bernick, B. A., et al., filed Apr. 1, 2020, 15 pages.
Notice of Allowance dated Mar. 17, 2021, in U.S. Appl. No. 16/837,937, Bernick, B. A., et al., filed Apr. 1, 2020, 7 pages.
Notice of Allowance dated Sep. 8, 2020, in U.S. Appl. No. 14/521,002, Bernick, B. A., et al., filed Oct. 22, 2014, 6 pages.
Bassi, P., and Kaur, G., "Innovations in bioadhesive vaginal drug delivery system," *Expert Opinion on Therapeutic Patents* 22(9):1019-1032, Taylor and Francis Ltd., United Kingdom (published online Aug. 2012, published in print Sep. 2012).
UNC School of Pharmacy, "Preparation of Suppositories," PharmLabs. unc.edu, accessed at http://pharmlabs.unc.edu/labs/suppository/inserting.htm on Apr. 16, 2021, 1 page.
Office Action dated Apr. 30, 2021, in U.S. Appl. No. 16/834,780, Bernick, B. A., et al., filed Apr. 30, 2021, 13 pages.
Office Action dated Apr. 30, 2021, in U.S. Appl. No. 16/875,030 Bernick, B. A., et al., filed Apr. 30, 2021, 17 pages.
Dugal et al., "Comparison of usefulness of estradiol vaginal tablets and estriol vagitories for treatment of vaginal atrophy" *Acta Obstericia et Gynecologia Scandinavica,* 79, 2000, pp. 293-297.
Rodriguez-Tenreiro, C. et al., "Cyclodextrin/carbopol micro-scale interpenetrating networks for drug delivery" *J. of Controlled Release* 123, 2007, pp. 56-66.
Rodriguez-Tenreiro, C. et al., "Estradiol sustained release from high affinity cyclodextrin hydrogels" *Eur. J. of Pharmaceutics and Biopharmaceutics* 66, 2007, 55-62.

\* cited by examiner

SOLUBLE ESTRADIOL CAPSULE FOR VAGINAL INSERTION

CROSS-REFERENCE TO RELATED APPLICATIONS

This application claims priority to the following U.S. patent applications: U.S. Provisional Application Ser. No. 61/661,302, entitled "ESTRADIOL FORMULATIONS," which was filed on Jun. 18, 2012; U.S. Provisional Application Ser. No. 61/662,265, entitled "PROGESTERONE FORMULATIONS," which was filed on Jun. 20, 2012; U.S. patent application Ser. No. 13/684,002, entitled "NATURAL COMBINATION HORMONE REPLACEMENT FORMULATIONS AND THERAPIES," which was filed Nov. 21, 2012; U.S. Provisional Application Ser. No. 61/745,313, entitled "SOLUBLE ESTRADIOL CAPSULE FOR VAGINAL INSERTION," which was filed on Dec. 21, 2012; U.S. Patent Application Serial No. PCT/US2013/023309, entitled "TRANSDERMAL HORMONE REPLACEMENT THERAPIES," which was filed Jan. 25, 2013; and U.S. patent application Ser. No. 13/843,428, entitled "NATURAL COMBINATION HORMONE REPLACEMENT FORMULATIONS AND THERAPIES," which was filed Mar. 15, 2013. All aforementioned applications are hereby incorporated by reference herein in their entirety.

BACKGROUND

Field

Postmenopausal women frequently suffer from certain vaginally localized states including, for example, atrophic vaginitis or vulvar and vaginal atrophy (hereinafter "vulvovaginal atrophy" or "VVA") with symptoms including, for example, dryness, itching, soreness, irritation, bleeding and dyspareunia; with urinary frequency, urgency, urinary discomfort and incontinence also occurring (singularly and collectively, "estrogen-deficient urinary state(s)"). For the sake of clarity, the terms "atrophic vaginitis" and vulvovaginal atrophy are used herein interchangeably. The molecular morphology of VVA is well known in the medical field.

Each of these VVA-related states, inter alia, are symptoms associated with decreased estrogenization of the vulvovaginal tissue, and can even occur in women treated with oral administration of an estrogen-based pharmaceutical drug product. Although VVA is most common with menopausal women, it can occur at any time in a woman's life cycle.

VVA-related states are generally treated with local administration of an estrogen-based natural or synthetic hormone in the form of a topically applied gel or cream, or through vaginal insertion of a compressed tablet. These forms of administration can provide low levels of circulating estrogen but are not intended to contribute to the treatment of other states related to estrogen deficiencies typically treated via administration of a systemically absorbed estrogen product. For example, such systemically absorbed products include orally administered formulations as well as creams, gels, sprays, and transdermally delivered products. However, vaginal gels and creams may rub, wear or wash off before the estrogen is fully absorbed into the local tissue. In addition, various commercially available estrogen-containing creams contain an alcohol such as benzyl alcohol and/or stearyl alcohol. The use of such products may result in itching or burning when applied. The above referenced vaginal creams and gels require insertion via a reusable vaginal applicator/plunger for which patients complain of difficulty to accurately dose, discomfort or pain upon insertion, and increased trauma to the genital mucosa all in relation to the vaginal applicator. Furthermore, the reusable applicator/plunger is also difficult to clean resulting in hygienic concerns as well as increased rates of infection all decreasing the ongoing compliance of the therapy.

Similarly, vaginal suppositories in the form of inserted tablets may not fully dissolve, reducing the effective dose of absorbed estrogen; may cause unwanted and unnecessary vaginal discharge; may cause an increase of vulvovaginal pruritus and/or back pain; and the insertion, itself, using the applicator provided with the reference-listed tableted drug, Vagifem® (Novo Nordisk; Princeton, N.J.), may cause a rupture of the vaginal fornix.

There has been at least one attempt at providing a soluble or suspended estrogen capsule for vaginal insertion as described in U.S. Pat. No. 6,060,077 (the '077 patent). The '077 patent provides for a non-systemic treatment for vaginal dryness in menopausal women using an immediate or slow-release formulation comprising a natural estrogen compound in solution or suspension in a lipophilic agent, a hydrophilic gel-forming bioadhesive agent, a gelling agent for the lipophilic agent, and a hydrodispersible agent in a hard or soft capsule. It is specifically stated that these formulations are designed to avoid systemic passage of estradiol following administration. Once in contact with vaginal secretions, these formulations require the presence of the hydrophilic gel-forming bioadhesive agent to react with the hydrodispersible agent to form an estrogen-containing emulsion to facilitate absorption. A practical issue arises when attempting to use this medicament when vaginal secretions are required to activate the formulation while the treatment is designed to treat vaginal dryness.

Accordingly, an estrogen-based vaginal suppository that provides an ease of administration/insertion, improved safety of insertion, lacking or minimizing vaginal discharge following administration, and that does not require vaginal secretions to activate the formulation could provide a more effective dosage form with improved efficacy, safety and patient compliance.

SUMMARY

According to various embodiments of this disclosure, encapsulated pharmaceutical formulations comprising solubilized estradiol are provided. Such formulations are encapsulated in soft capsules which are vaginally inserted for the treatment of vulvovaginal atrophy.

BRIEF DESCRIPTION OF THE DRAWINGS

The subject matter of the present invention is particularly pointed out and distinctly claimed below. A more complete understanding of the present invention, however, may best be obtained by referring to the detailed description and claims when considered in connection with the figures, wherein like numerals denote like elements and wherein:

DETAILED DESCRIPTION OF THE ILLUSTRATED EMBODIMENTS

Definitions

Figure 1:
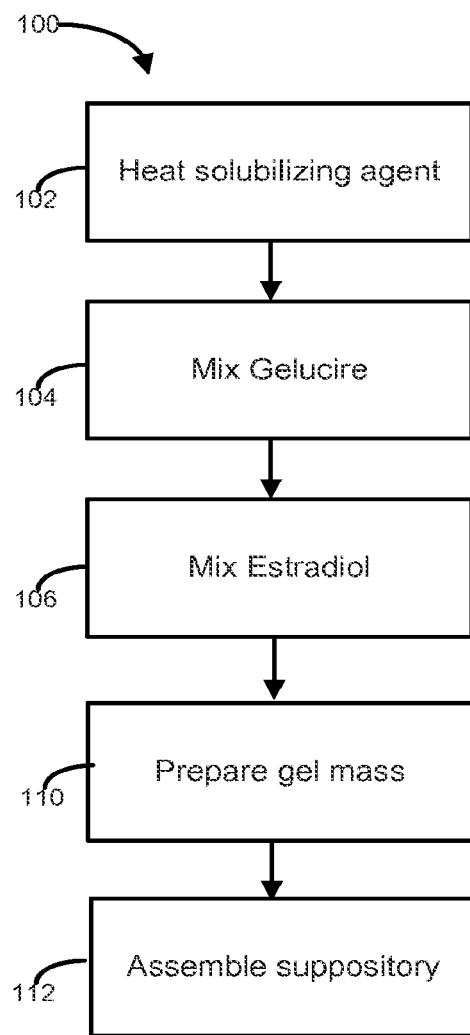
FIG. 1 is a flow diagram illustrating a process in accordance with various embodiments of the invention.

The term "active pharmaceutical ingredient" as used herein, means the active compound(s) used in formulating a drug product.

The term "AUC," as used herein, refers to the area under the curve that represents changes in blood concentration of an active pharmaceutical ingredient (e.g., estradiol, which is also referred to in the literature as 17β-estradiol, oestradiol, or E2) over time.

The term "bioavailability", as used herein means the concentration of an active ingredient (e.g., estradiol) in the blood (serum or plasma). The relative bioavailability may be measured as the concentration in the blood (serum or plasma) versus time. Pharmacokinetic (PK) indicators that may be used to measure and assess bioavailability are determined by suitable metrics including AUC, Cmax, and, optionally, Tmax.

The term "bioequivalent" means that a test drug product provides similar bioavailability compared to a reference drug product pursuant to the criteria set forth for bioequivalence by the United States Food and Drug Administration, as amended. In general, the bioavailability of an active pharmaceutical ingredient in a bioequivalent drug product is 80 to 125% of the bioavailability of the active pharmaceutical ingredient of the reference drug product concerning AUC and Cmax.

The term "bio-identical hormones", as used herein, means those synthetically-derived compounds which are identical in chemical structure to the hormones naturally produced in vivo. These natural or bio-identical hormones are synthesized from various ingredients to match the chemical structure and effect of estradiol or estrone, or estriol (the 3 primary estrogens).

The term, "Cmax" as used herein, refers to the maximum value of blood concentration shown on the curve that represents changes in blood concentrations of an active pharmaceutical ingredient (e.g., estradiol) over time.

The term "co-administered" as used herein, means that two drug products are administered simultaneously or sequentially on the same or different days.

The term "drug product" as used herein means at least one active pharmaceutical ingredient in combination with at least one excipient and provided in unit dosage form.

The term "excipients," as used herein, refer to non-active pharmaceutical ingredients such as carriers, solubilizing agents, oils, lubricants and others used in formulating pharmaceutical products. They are generally safe for administering to animals, including humans, according to established governmental standards, including those promulgated by the United States Food and Drug Administration.

The term "natural," as used herein with reference to hormones discussed herein, means bio-identical hormones synthesized to match the chemical structure and effect of those that occur naturally in the human body (endogenous). An exemplary natural estrogen is estradiol (also described as 17β-estradiol and E2).

The term "medium chain," as used herein means any medium chain carbon-containing substance, including C4-C18, and including C6-C12 substances, fatty acid esters of glycerol, fatty acids, and mono-, di-, and triglycerides of such substances. For further illustration, C6-C14, C6-C12 fatty acids, and C8-C10 fatty acids are all medium chain fatty acids and may be used in instances in which this specification calls for use of medium chain fatty acids, e.g., medium chain fatty acid esters of glycerol or other glycols.

The term "reference listed drug product" as used herein means Vagifem®.

The term "solubilizer," as used herein, means any substance or mixture of substances that may be used to enhance the solubility of estradiol, including, for example and without limitation, appropriate pharmaceutically acceptable excipients, such as solvents, co-solvents, surfactants, emulsifiers, oils and carriers.

The term "treatment", as used herein, or a derivative thereof, contemplates partial or complete inhibition of the stated disease state or condition when a formulation as described herein is administered prophylactically or following the onset of the disease state for which such formulation is administered. For the purposes of the present disclosure, "prophylaxis" refers to administration of the active ingredient(s) to an animal, typically a human, to protect the animal from any of the disorders set forth herein, as well as others.

The term, "Tmax" as used herein, refers to the time that it takes for an active pharmaceutical ingredient (e.g., estradiol) and/or estrone blood concentrations to reach the maximum value.

Description

Provided herein are pharmaceutical formulations comprising solubilized estradiol (in various embodiments, at least 90% in solution); providing said formulations do not embrace within the fill one or more of the following components: a hydrophilic gel-forming bioadhesive (e.g., mucoadhesive) agent; a lipophilic agent; a gelling agent for the lipophilic agent, and/or a hydrodispersible agent. The hydrophilic gel-forming bioadhesive agent may provide or exclude one or more of a: carboxyvinylic acid; hydroxypropylcellulose; carboxymethylcellulose; gelatin; xanthane gum; guar gum; aluminum silicate; or mixtures thereof. The lipophilic agent may provide or exclude one or more of a: liquid triglyceride; solid triglyceride (with a melting point of about 35° C.); carnauba wax; cocoa butter; or mixtures thereof. The gelling agent may provide or exclude one or more of a hydrophobic colloidal silica. The hydrodispersible agent may provide or exclude one or more of a: polyoxyethylene glycol; polyoxyethylene glycol 7-glyceryl-cocoate and mixtures thereof.

Generally, the pharmaceutical formulations described herein are prepared and administered as filled capsules, typically soft capsules of one or more materials well known in the art including, for example and without limitation, soft gelatin capsules. However, in various embodiments, pharmaceutical formulations described herein are prepared as a gel, cream, ointment, transdermal delivery system or like preparation.

Other aspects of the present disclosure include the use of formulations as described herein for the treatment of vulvovaginal atrophy including the treatment of at least one VVA symptom including, for example and without limitation, dryness, itching, soreness, irritation, bleeding and dyspareunia.

Another aspect of the present disclosure provides uses of the formulations described herein for the treatment of estrogen-deficient urinary states.

Another aspect of the present disclosure provides alcohol-free or substantially alcohol-free formulations, and uses thereof. Among others, the formulations offer improved comfort during use, thus tending to enhance patient compliance.

The methods of treatment described herein are generally administered to a human female.

A further aspect of the present invention provides formulations of the present invention wherein circulating blood level concentrations following administration of a formulation of the present invention are bioequivalent to circulating blood level concentrations following administration of the reference listed drug product, as determined through the completion of a bioequivalence clinical study.

The formulations of the present disclosure may also be vaginally administered with or without the co-administration of an orally administered estrogen-based (or progestin-based or progestin- and estrogen-based) pharmaceutical drug product, or patch, cream, gel, spray, transdermal delivery system or other parenterally-administered estrogen-based pharmaceutical drug product, each of which can include natural, bio-similar, or other synthetic or derived estrogens and/or an administered progestin. As used herein, the term "progestin" means any natural or man-made substance that has pharmacological properties similar to progesterone.

Modulation of circulating estrogen levels provided via the administration of a formulation of the present disclosure, if any, are not intended to be additive to any co-administered estrogen product and its associated circulating blood levels.

The timing of administration of a formulation of the present disclosure may be conducted by any safe means as prescribed by an attending physician. Typically, a patient will insert one capsule intra-vaginally each day for 14 days, then one capsule twice weekly for the remaining time prescribed by such physician. Intra-vaginal insertion may be via the use of an applicator or without an applicator via use of the patient's digits. Use of an applicator or otherwise requires due care as to not puncture or tear surrounding tissue.

Estradiol dosage strengths can vary. For formulations of the present disclosure, estradiol (or estradiol equivalent to the extent such estradiol is in a hydrated or other form requiring compensation therefore) dosage strength of is at least about 1 microgram (mcg), at least about 2.5 mcg; at least about 5 mcg; at least about 10 mcg, from about 1 mcg to about 10 mcg, from about 10 mcg to about 25 mcg, about 1 mcg, about 2.5 mcg, about 5 mcg, about 10 mcg and about 25 mcg. To protect against adverse effects of estradiol, the lowest possible dose should be used for treatment of VVA and other states set forth herein. In one embodiment, the dosage is about 10 mcg; in another the dosage is about 25 mcg.

Figure 2:
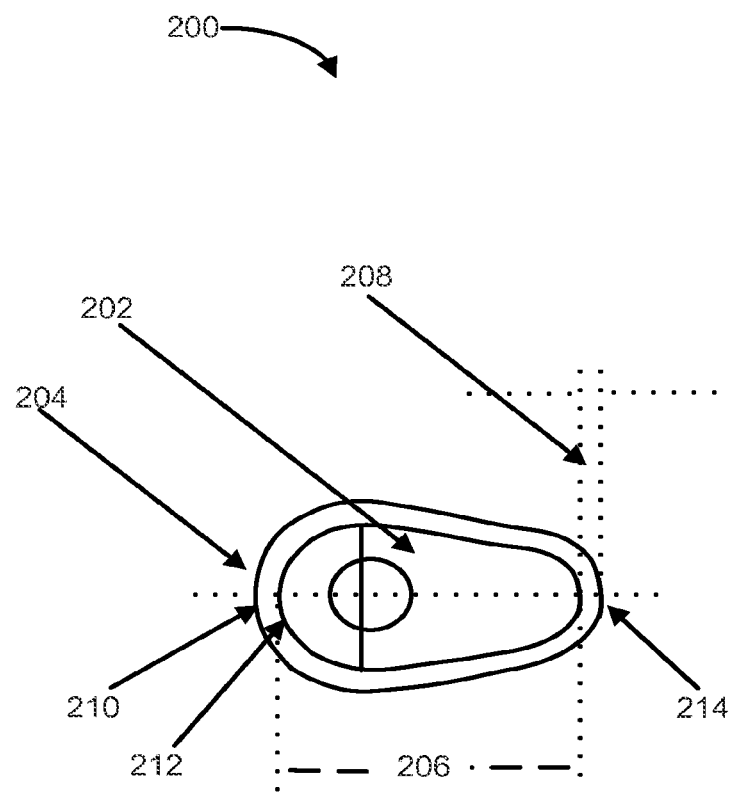
FIG. 2 illustrates a suppository in accordance with various embodiments of the invention.

Also provided are soft capsules designed for ease of insertion and to hold the capsule in place until the contents therein are completely released. In various embodiments, softgel capsules in accordance with various embodiments are sized to comfortably fit within a human vagina. Thus, the softgel capsules may comprise any dimension capable of fitting into a human vagina. With reference to FIG. 2, softgel capsule 200 is illustrated. Softgel capsule 200 comprises fill material 202 and gelatin 204. Gelatin 204 has a thickness represented by space 208. Space 208 comprises a distance of 0.108 inches. The distance from one end of softgel capsule 200 to another is represented by space 206. Space 206 comprises a distance of 0.690 inches. The size of softgel capsule 200 may also be described by the arc swept by a radius of a given length. For example, arc 210, which is defined by the exterior of gelatin 204, is an arc swept by a radius of 0.189 inches. Arc 212, which is defined by the interior of gelatin 204, is an arc swept by a radius of 0.0938 inches. Arc 214, which is defined by the exterior of gelatin 204 opposite arc 210, is an arc swept by a radius of 0.108 inches.

Estradiol can be formulated pursuant to the teachings below. These formulations can be prepared for vaginal insertion in a single unit dosage form or as otherwise specified herein.

In various embodiments, estradiol is solubilized at least once during manufacturing and, in various embodiments, estradiol is solubilized at one point following administration. Solubility may be expressed as a mass fraction (% w/w). As used herein, the term "soluble" or "solubilized" means that the estradiol is: at least about 85% soluble, at least 90% soluble, at least 95% soluble and, frequently, is 100% soluble. % Solubility is expressed herein as a mass fraction (% w/w, also referred to as wt %).

Upon release of the fill into the vaginal canal following insertion of a capsule of the present disclosure, estradiol may be locally absorbed into body tissues.

In various embodiments, the solubilizing agent is selected from at least one of a solvent or co-solvent. Suitable solvents and co-solvents include any mono-, di- or triglyceride and glycols, and combinations thereof.

Solubilized estradiol of the present disclosure is prepared via blending estradiol with a pharmaceutically acceptable solubilizing agent including for example and without limitation, at least one medium chain fatty acid such as medium chain fatty acids consisting of at least one mono-, di-, or triglyceride, or derivatives thereof, or combinations thereof (collectively, "glycerides"). In various embodiments, solubilized estradiol of the present disclosure may also comprise at least one glycol or derivatives thereof or combinations thereof (collectively, "glycols") and/or combinations of such at least one glyceride and glycol. Glycols may be used as solubilizing agents and/or to adjust viscosity and, thus, may be considered thickening agents, as discussed further herein. Optionally added are other excipients including, for example and without limitation, anti-oxidants, lubricants and the like. Sufficient solubilizing agent(s) is/are used to solubilize estradiol.

Pharmaceutically acceptable solubilizing agents include, for example and without limitation, the use of at least one of a caproic fatty acid; a caprylic fatty acid; a capric fatty acid; a tauric acid; a myristic acid; a linoleic acid; a succinic acid; a glycerin; mono-, di-, or triglycerides and combinations and derivatives thereof; a polyethylene glycol; a polyethylene glycol glyceride (GELUCIRE (polyethylene glycol glyceride) GATTEFOSSE SAS, Saint-Priest, France); which can be used herein as a solubilizing agent or as an anionic surfactant); a propylene glycol; a caprylic/capric triglyceride (MIGLYOL (caprylic/capric triglyceride)); SASOL Germany GMBH, Hamburg); MIGLYOL includes MIGLYOL 810 (caprylic/capric triglyceride), MIGLYOL 812 (caprylic/capric triglyceride), MIGLYOL 816 (caprylic/capric triglyceride) and MIGLYOL 829 (caprylic/capric/succinic triglyceride)); a caproic/caprylic/capric/lauric triglyceride; a caprylic/capric/linoleic triglyceride; a caprylic/capric/succinic triglyceride; a propylene glycol monocaprylate; propylene glycol monocaprate; (CAPMUL PG-8 (propylene glycol monocaprylate) and CAPMUL PG-10 (propylene glycol monocaprate); the CAPMUL brands are owned by ABITEC, Columbus Ohio); a propylene glycol mono- and dicaprylate; a propylene glycol mono- and dicaprate; medium chain mono- and di-glycerides (CAPMUL MCM (medium chain mono- and diglycerides)); a diethylene glycol mono ester (including 2-(2-Ethoxyethoxy)ethanol: TRANSCUTOL (diethylene glycol monoethyl ether)); a diethylene glycol monoethyl ether; glyceryl mono- and di-caprylates; propylene glycol; 1,2,3-propanetriol (glycerol, glycerin, glycerine) esters of saturated coconut and palm kernel oil and derivatives thereof; triglycerides of fractionated vegetable fatty acids, and combinations and derivatives thereof. In various embodiments, propylene glycol is used in a cream or ointment.

These solubilizers, as defined herein, and combinations thereof, can be used to form solubilized estradiol formulations of the present disclosure.

At least one anionic and/or non-ionic surfactant can be used in additional embodiments of the presently disclosed formulations containing solubilized estradiol.

Exemplary non-ionic surfactants may include, for example and without limitation, one or more of oleic acid, linoleic acid, palmitic acid, and stearic acid. In further embodiments, the non-ionic surfactant may comprise polyethylene sorbitol esters, including polysorbate 80, which is commercially available under the trademark TWEEN 80 (polysorbate 80) (Sigma Aldrich, St. Louis, Mo.). Polysorbate 80 comprises approximately 60%-70% oleic acid with the remainder comprising primarily linoleic acids, palmitic acids, and stearic acids. Polysorbate 80 may be used in amounts ranging from about 5 to 50%, and in certain embodiments, about 30% of the formulation total mass. In various other embodiments, the non-ionic surfactant is selected from one or more of glycerol and polyethylene glycol esters of long chain fatty acids, for example, lauroyl macrogol-32 glycerides and/or lauroyl polyoxyl-32 glycerides, commercially available as GELUCIRE, including, for example, GELUCIRE 39/01 (glycerol esters of saturated C12-C18 fatty acids), GELUCIRE 43/01 (hard fat NF/JPE) and GELUCIRE 50/13 (stearoyl macrogol-32 glycerides EP, stearoyl polyoxyl-32 glycerides NF, stearoyl polyoxylglycerides (USA FDA IIG)). These surfactants may be used at concentrations greater than about 0.01%, and typically in various amounts of about 0.01%-10.0%, 10.1%-20%, and 20.1%-30%.

Ratios of solubilizing agent(s) to surfactant(s) can vary depending upon the respective solubilizing agent(s) and the respective surfactant(s) and the desired physical characteristics of the resultant formulation of solubilized estradiol. For example and without limitation, CAPMUL MCM and a non-ionic surfactant can be used at ratios including 65:35, 70:30, 75:25, 80:20, 85:15 and 90:10. Other non-limiting examples include: CAPMUL MCM and GELUCIRE 39/01 can be used in ratios including, for example and without limitation, 6:4, 7:3, and 8:2; CAPMUL MCM and GELUCIRE 43/01 can be used in ratios including, for example and without limitation, 7:3, and 8:2; CAPMUL MCM and GELUCIRE 50/13 can be used in ratios including, for example and without limitation, 7:3, and 8:2, and 9:1.

Another exemplary non-ionic surfactant includes PEG-6 palmitostearate and ethylene glycol palmitostearate, which is available commercially as TEFOSE 63 ("Tefose 63"; GATTEFOSSE SAS, Saint-Priest, France) which can be used with, for example, CAPMUL MCM having ratios of MCM to TEFOSE 63 of, for example, 8:2 and 9:1. Additional examples of solubilizing agents with non-ionic surfactants include, for example, MIGLYOL 812:GELUCIRE 50/13 and MIGLYOL 812:TEFOSE 63.

Anionic surfactants are well known and can include, for example and without limitation: ammonium lauryl sulfate, dioctyl sodium sulfosuccinate, perfluoro-octane sulfonic acid, potassium lauryl sulfate and sodium stearate.

Non-ionic and/or anionic surfactants can be used alone or with at least one solubilizing agent or can be used in combination with other surfactants. Accordingly, such surfactants, or any other excipient as set forth herein, should be used to provide solubilized estradiol, upon release from a vaginally-inserted capsule, with consistency of the solubilized estradiol that promotes absorption and minimizes vaginal discharge, particularly when compared to the vaginal discharge frequently occurring following use of a VAGIFEM tablet.

Moreover, the estradiol in the formulations disclosed herein need not be fully solubilized (e.g., at least 98% in solution) at the time of administration/insertion but, rather, needs to be substantially solubilized at the time of release from the vaginally-inserted capsule. As such, the solubilizing agents taught herein, with or without additional excipients other than the solubilizing agents, may be in the liquid or semi-solid form upon administration providing the estradiol containing solubilizing agents and other excipients permit flow to fill capsules. To the extent the estradiol is not fully solubilized at the time of administration/insertion, the estradiol should be substantially solubilized at a temperature of about 37° C. (e.g., body temperature) and, generally, at a pH of about 4.5. In another embodiment, at least one thickening agent may be added to formulations of the present disclosure. The viscosity of the solubilized estradiol may depend upon the solubilizing agent(s) used, the addition of other excipients to the formulation preparation and the desired or required final viscosity required to optimize absorption of the solubilized estradiol. In certain embodiments, the surfactant(s) referenced herein above may provide thickening of the solubilized estradiol such that, upon release, will aid the estradiol in being absorbed by the vaginal mucosa while minimizing vaginal discharge, particularly when compared to the vaginal discharge frequently occurring following use of a Vagifem tablet. Examples of other such thickening agents include, for example and without limitation, hard fats; propylene glycol; a mixture of hard fat EP/NF/JPE, glyceryl ricinoleate, ethoxylated fatty alcohols (ceteth-20, steareth-20) EP/NF (commercially available as OVUCIRE 3460 (mixture of hard fat EP/NF/JPE (and) glyceryl ricinoleate (and) ethoxylated fatty alcohols (ceteth-20, steareth-20) EP/NF) (Gattefosse, Saint-Priest France); a mixture of hard fat EP/NF/JPE, glycerol monooleate (type 40) EP/NF (commercially available as OVUCIRE WL 3264 (mixture of hard fat EP/NF/JPE (and) glycerol monooleate (type 40) EP/NF); a mixture of hard fat EP/NF/JPE, glyceryle monooleate (type 40) EP/NF (commercially available as OVUCIRE WL 2944 (mixture of hard fat EP/NF/JPE (and) glyceryle monooleate (type 40) EP/NF)); and a mixture of various hard fats (commercially available as WITESPOL (hard fats); Sasol Germany GmbH, Hamburg). In various embodiments, the viscosity of formulations in accordance with various embodiments may comprise from about 50 cps to about 1000 cps at 25° C.

In other embodiments, one or more muco-adherent agents may be used to assist with mucosal absorption of the solubilized estradiol. For example, polycarbophil may be used as an acceptable muco-adherent agent. Other agents include, for example and without limitation, poly (ethylene oxide) polymers having a molecular weight of from about 100,000 to about 900,000, chitosans carbopols including polymers of acrylic acid crosslinked with allyl sucrose or allyl pentaerythritol, polymers of acrylic acid and C10-C30 alkyl acrylate crosslinked with allyl pentaerythritol, carbomer homopolymer or copolymer that contains a block copolymer of polyethylene glycol and a long chain alkyl acid ester and the like. Various hydrophilic polymers and hydrogels may be used. In various embodiments, the hydrophilic polymer will swell in response to contact with vaginal or other bodily secretions, enhancing moisturizing and muco-adherent effects. The selection and amount of hydrophilic polymer may be based on the selection and amount of pharmaceutically acceptable solubilizing agent chosen. The formulation includes a hydrophilic polymer but optionally excludes a gelling agent. In embodiments having a hydrogel, from about 5% to about 10% of the total mass may comprise the hydrophilic polymer. In further embodiments, hydrogels may be employed. A hydrogel may comprise chitosan, which swell in response to contact with water. In various embodiments, a cream formulation may comprise PEG-90M.

In additional embodiments, formulations of the present disclosure may include one or more thermoreversible gels, typically of the hydrophilic nature including for example and without limitation, hydrophilic sucrose and other saccharide-based monomers (U.S. Pat. No. 6,018,033, which is herein incorporated by reference).

In other embodiments, a lubricant may be used. Any suitable lubricant may be used, such as for example lecithin. Lecithin may comprise a mixture of phospholipids.

In additional embodiments, an antioxidant is used. Any suitable antioxidant may be used such as, for example and without limitation, butylated hydroxytoluene.

In various embodiments, a pharmaceutical formulation comprises about 20% to about 80% solubilizing agent by weight, about 0.1% to about 5% lubricant by weight, and about 0.01% to about 0.1% antioxidant by weight.

The choice of excipient will, to a large extent, depend on factors such as for example and without limitation, the effect of the excipient on solubility and stability. Additional excipients used in various embodiments may include colorants and preservatives. Colorants, for example, may comprise about 0.1% to about 2% by weight. Preservatives may, for example and without limitation, comprise methyl and propyl paraben, for example, in a ratio of about 10:1, and at a proportion of about 0.005% and 0.05% by weight.

As is with all solubilizing agents, excipients and any other additives used in the formulations described herein, each is to be non-toxic, pharmaceutically acceptable and compatible with all other ingredients used.

Further provided herein are methods for the treatment of VVA and/or estrogen-deficient urinary states comprising administering to a female, typically a human, in need of treatment a non-toxic and pharmaceutically effective dose of a formulation as further provided herein.

As referenced above, the formulations of the present disclosure are generally vaginally administered via capsules such as soft capsules, including soft gelatin capsules. It is desirable to prepare these soft capsules such that they disintegrate to the extent that substantially all of the solubilized estradiol is released upon disintegration, providing rapid absorption of the solubilized estradiol and minimal to no capsule residue.

Additional objects of the present disclosure include: providing increased patient ease of use while potentially minimizing certain side effects from inappropriate insertion, minimizing incidence of vulvovaginal mycotic infection compared to incidence of vulvovaginal mycotic infection due to usage of Vagifem and other currently available products and; decreased resultant genital pruritus compared to the genital pruritus and/or back pain that may be generated via the use of Vagifem and other currently available products. In illustrative embodiments of the invention, oils are used as solubilizing agents to solubilize estradiol and include medium chain fatty acid esters, (e.g., esters of glycerol, polyethylene glycol, or propylene glycol) and mixtures thereof. In illustrative embodiments, the medium chain fatty acids are C6 to C14 or C6 to C12 fatty acids. In illustrative embodiments, the medium chain fatty acids are saturated, or predominantly saturated, e.g., greater than about 60% or greater than about 75% saturated. In illustrative embodiments, estradiol is soluble in the oils at room temperature, although it may be desirable to warm certain oils initially during manufacture to improve viscosity. In illustrative embodiments, the oil or oil/thickening agent is liquid at between room temperature and about 50° C., e.g., at or below 50° C., at or below 40° C., or at or below 50° C. In illustrative embodiments, GELUCIRE 44/14 (lauroyl macrogol-32 glycerides EP lauroyl polyoxyl-32 glycerides NF lauroyl polyoxylglycerides (USA FDA IIG)) is heated to about 65° C. and CAPMUL MCM is heated to about 40° C. to facilitate mixing of the oil and non-ionic surfactant, although such heating is not necessary to dissolve the estradiol. In illustrative embodiments, the solubility of estradiol in the oil (or oil/surfactant) is at least about 0.5 wt %, e.g., 0.8 wt % or higher, or 1.0 wt % or higher. Illustrative examples of mono- and diglycerides of medium chain fatty acids include, among others, CAPMUL MCM, CAPMUL MCM C10 (glyceryl monocaprate), CAPMUL MCM C8 (glyceryl monocaprylate), and CAPMUL MCM C8 EP (glyceryl monocaprylate). These oils are C8 and C10 fatty acid mono- and diglycerides. Illustrative examples of oils that are triglycerides of medium chain fatty acids include, among others, MIGLYOL 810 and M IGLYOL 812. Illustrative examples of oils that are medium chain fatty acid esters of propylene glycol include, among others, CAPMUL PG-8, CAPMUL PG-2L EP/NF (propylene glycol dilaurate), CAPMUL PG-8 NF (propylene glycol monocaprylate), CAPMUL PG-12 EP/NF (propylene glycol monolaurate) and CAPRYOL (propylene glycol monocaprylate (type II) NF). Other illustrative examples include MIGLYOL 840 (propylene glycol dicaprylate/dicaprate).

Illustrative examples of oils that are medium chain fatty acid esters of polyethylene glycol include, among others, GELUCIRE 44/14 (PEG-32 glyceryl laurate EP), which is polyethylene glycol glycerides composed of mono-, di- and triglycerides and mono- and diesters of polyethylene glycol.

These illustrative examples comprise predominantly medium chain length, saturated, fatty acids (i.e., greater than 50% of the fatty acids are medium chain saturated fatty acids); specifically predominantly C8 to C12 saturated fatty acids.

It will be understood that commercially available fatty acid esters of glycerol and other glycols are often prepared from natural oils and therefore may comprise components additional to the fatty acid esters that comprise the predominant (by weight) component(s) and that therefore are used to characterize the product. Such other components may be, e.g., other fatty acid triglycerides, mono- and diesters, free glycerol, or free fatty acids. So, for example, when an oil/solubilizing agent is described herein as a saturated C8 fatty acid mono- or diester of glycerol, it will be understood that the predominant component of the oil, i.e., >50 wt % (e.g., >75 wt %, >85 wt % or >90 wt %) are caprylic monoglycerides and caprylic diglycerides. For example, the Technical Data Sheet by ABITEC for CAPMUL MCM C8 describes CAPMUL MCM C8 as being composed of mono and diglycerides of medium chain fatty acids (mainly caprylic) and describes the alkyl content as <=1% C6, >=95% C8, <=5% C10, and <=1.5% C12 and higher By way of further example, MIGLYOL 812 is generally described as a C8-C10 triglyceride because the fatty acid composition is at least about 80% caprylic (C8) acid and capric (C10) acid. However, it can also comprise small amounts of other fatty acids, e.g., less than about 5% of caproic (C6) acid, lauric (C12) acid, and myristic (C14) acid.

Specifically, a product information sheet for MIGLYOL by SASOL provides the composition of fatty acids as follows:

| Tests | 810 | 812 | 818 | 829 | 840 |
|---|---|---|---|---|---|
| Caproic acid (C6:0) | max. 2.0 | max. 2.0 | max. 2 | max. 2 | max. 2 |
| Caprylic acid (C8:0) | 65.0-80.0 | 50.0-65.0 | 45-65 | 45-55 | 65-80 |
| Capric acid (C10:0) | 20.0-35.0 | 30.0-45.0 | 30-45 | 30-40 | 20-35 |
| Lauric acid (C12:0) | max. 2 | max. 2 | max. 3 | max. 3 | max. 2 |
| Myristic acid (C14:0) | max. 1.0 | max. 1.0 | max. 1 | max. 1 | max. 1 |
| Linoleic acid (C18:2) | — | — | 2-5 | — | — |
| Succinic acid | — | — | — | 15-20 | — |

So, if an embodiment of this invention is described as comprising (or consisting essentially of) a capsule shell, estradiol solubilized in C8-C10 triglycerides, and a thickening agent, it will be understood that the fatty acid esters component of the formulation may be, e.g., MIGLYOL 812 or a similar product.

By way of further illustration, GELUCIRE 44/14 is generally described as lauroyl polyoxyl-32 glycerides, i.e., polyoxyethylene 32 lauric glycerides (which is a mixture of mono-, di-, and triesters of glycerol and mono- and diesters of PEGs) because the fatty acid composition is 30 to 50% lauric acid and smaller amounts of other fatty acids, e.g., up to 15% caprylic acid, up to 12% capric acid, up to 25% myristic acid, up to 25% palmitic acid, and up to 35% stearic acid. The product may also contain small amounts of non-esterified glycols. So, if an embodiment of this invention is described as comprising (or consisting essentially of) a capsule shell, estradiol solubilized in triglycerides, and a thickening agent that is a non-ionic surfactant comprising C8 to C18 fatty acid esters of glycerol and polyethylene glycol, it will be understood that the thickening agent component of the formulation may be, e.g., GELUCIRE 44/14 or a similar product.

Similarly, if an embodiment of this invention is described as comprising (or consisting essentially of) a capsule shell, estradiol solubilized in triglycerides, and a thickening agent that is a non-ionic surfactant comprising PEG-6 stearate, ethylene glycol palmitostearate, and PEG-32 stearate, it will be understood that the thickening agent component of the formulation may be, e.g., TEFOSE 63 or a similar product.

Mixtures of medium chain fatty acid glycerides, e.g., C6-C12, C8-C12, or C8-C10 fatty acid mono- and diglycerides or mono-, di-, and triglycerides are very well suited for dissolving estradiol; good results have been obtained with an oil that is predominantly a mixture of C8-C10 saturated fatty acid mono- and diglycerides. Longer chain glycerides appear to be not as well suited for dissolution of estradiol.

High solubility of estradiol has been obtained in 2-(2-Ethoxyethoxy)ethanol, e.g., TRANSCUTOL and in Propylene glycol monocaprylate, e.g., Capryol™ 90 (Gattefosse).

In various embodiments, the solubilizing agent is selected from at least one of a solvent or co-solvent. Suitable solvents and co-solvents include any mono-, di- or triglyceride and glycols, and combinations thereof.

In addition, other solubilizers include, for example and without limitation, glyceryl mono- and di-caprylates, propylene glycol and 1,2,3-propanetriol (glycerol, glycerin, glycerine).

Illustrative Drug Product(s)

Through extensive trial-and-error testing of various fatty acid esters of glycerol and other glycols, embodiments of the invention have been invented that have one or more favorable characteristics for development as a human drug product. Such favorable characteristics include, e.g., lack of or reduction of irritation relative to otherwise similar formulations, lack of or reduction in vaginal discharge of drug product relative to otherwise similar formulations, lack of or reduction of drug product residue inside the vagina, etc. Non-irritating formulations are formulations that in most uses in most patients, when used as prescribed, does not cause pain, soreness, swelling or irritation inside the vagina such that most patients do not go off treatment prior to completion of a prescribed course of therapy. Non-irritating formulations are also formulations that are non-irritating, as described in the preceding sentence, relative to competing products such as tablets, creams, or other intravaginal estrogen delivery forms. Such illustrative drug products are also easily self-administered by a patient in any position by inserting the encapsulated formulation digitally approximately 2 inches into her vagina without a need for an applicator and with minimal to no corresponding discharge.

Formulations that do not create a residue are formulations that are absorbed and/or dispersed without resulting in particulates or other unpleasant remains of non-absorbed or non-dispersed drug product. Again, lack of residue can be relative to competing products.

Formulations that do not discharge from the vagina are formulations that do not flow or drip out of the vagina. Again, lack of discharge can be relative to competing products.

Such embodiments include an encapsulated liquid pharmaceutical formulation for intra-vaginal delivery of estradiol, said formulation comprising estradiol that is at least about 90% solubilized in one or more C6 to C14 fatty acid mono-, di-, or triesters of glycerol and a thickening agent.

A more specific such embodiment is such formulation wherein the estradiol is solubilized (e.g., >90% solubilized) in one or more C6 to C12 fatty acid mono-, di-, or triesters of glycerol, e.g., one or more C6 to C14 triglycerides, e.g., one or more C6 to C12 triglycerides, such as one or more C8-C10 triglycerides.

In such general and more specific embodiments, the thickening agent can be a non-ionic surfactant, e.g., a polyethylene glycol saturated or unsaturated fatty acid ester or diester. In certain such embodiments, the non-ionic surfactant comprises a polyethylene glycol long chain (C16-C20) fatty acid ester and further comprises an ethylene glycol long chain fatty acid ester, such as PEG-fatty acid esters or diesters of saturated or unsaturated C16-C18 fatty acids, e.g., oleic, lauric, palmitic, and stearic acids. In certain such embodiments, the non-ionic surfactant comprises a polyethylene glycol long chain saturated fatty acid ester and further comprises an ethylene glycol long chain saturated fatty acid ester, such as PEG- and ethylene glycol-fatty acid esters of saturated C16-C18 fatty acids, e.g., palmitic and stearic acids. Such non-ionic surfactant can comprise PEG-6 stearate, ethylene glycol palmitostearate, and PEG-32 stearate, such as but not limited to TEFOSE 63.

In certain such embodiments, the non-ionic surfactant employed as the thickening agent is not hydrophilic and has good emulsion properties. An illustrative example of such surfactant is TEFOSE 63, which has a HLB value of about 9-10.

As noted above, such formulations are liquid at room temperature, not gels, hard fats, or any other solid form. The thickening agent serves to increase viscosity, e.g., up to 10,000 cP (10,000 mPa-s), typically to no more than 5000 cP, and more typically to between 50 and 1000 cP. In some such embodiments, the non-ionic surfactant, e.g., GELUCIRE or TEFOSE, may be solid at room temperature and require melting to effect mixing with the estradiol solubilized in fatty acid-glycol esters but the resultant formulation is advantageously liquid, not solid.

The formulation of such embodiments is typically encapsulated in a soft gelatin capsule or other soft capsule.

Typically, such formulations do not comprise a bioadhesive (i.e., mucoadhesive) agent, a gelling agent, or a dispersing agent, or, at least, do not comprise one or two of such components.

In more specific such formulations, the capsule shell, the active pharmaceutical ingredient, the fatty acid esters and the thickening agent are the only essential ingredients. Non-essential ingredients, e.g., colorants, antioxidants or other preservatives, etc., may, of course, be included but other ingredients in amounts that would materially change the solubility of the estradiol, the PK of the encapsulated formulation, the irritancy, vaginal discharge, intravaginal residue, etc., e.g., other oils or fatty acid esters, lecithin, muco-adherent agents, gelling agents, dispersing agents, or the like would not be included. Such embodiments of the invention may be described as consisting essentially of the capsule shell, the active pharmaceutical ingredient, the fatty acid esters and the thickening agent, as described in the immediately preceding paragraphs describing illustrative embodiments discovered to have favorable characteristics.

As an example of such embodiments discovered to have such favorable characteristics is mentioned the product identified in Example 3, below, as "Trial 5".

EXAMPLES

In various embodiments, a vehicle system is created by dissolving an active pharmaceutical ingredient (e.g., estradiol) in one or more pharmaceutically acceptable solubilizing agents. A vehicle system may then be combined with a gel mass to create a final formulation suitable for use in, for example, a vaginal suppository. In that regard, in various embodiments, one or more vehicle systems may be combined with one or more gel masses. Other excipients may also be included in the vehicle system in various embodiments.

Example 1

Formulation: Vehicle System

In various embodiments, estradiol active pharmaceutical ingredient is procured and combined with one or more pharmaceutically acceptable solubilizing agents. Estradiol may be in micronized form or non-micronized form. In various embodiments, the final formulation comprises estradiol in a dosage strength of from about 1 mcg to about 25 mcg.

Estradiol is combined with various pharmaceutically acceptable solubilizing agents in various embodiments. As described above, CAPMUL MCM, MIGLYOL 812, GELUCIRE 39/01, GELUCIRE 43/01, GELUCIRE 50/13, and TEFOSE 63(\may, alone or in various combinations, be used as a pharmaceutically acceptable solubilizing agent in connection with estradiol.

Solubility of estradiol may affect final formulation stability and uniformity, so care should be taken when selecting an appropriate vehicle system. It is noted that surfactants are typically amphiphilic molecules that contain both hydrophilic and lipophilic groups. A hydrophilic-lipophilic balance ("HLB") number is used as a measure of the ratio of these groups. It is a value between 0 and 20 which defines the affinity of a surfactant for water or oil. HLB numbers are calculated for nonionic surfactants, and these surfactants have numbers ranging from 0-20. HLB numbers>10 have an affinity for water (hydrophilic) and number<10 have an affinity of oil (lipophilic).

In that regard, GELUCIRE 39/01 and GELUCIRE 43/01 each have an HLB value of 1. GELUCIRE 50/13 has an HLB value of 13. TEFOSE 63 has an HLB value of between 9 and 10.

Various combinations of pharmaceutically acceptable solubilizing agents were combined with estradiol and examined. TABLE 1 contains the results. TABLE 1 contains the following abbreviations: CAPMUL MCM ("MCM"), GELUCIRE 39/01 ("39/01"), GELUCIRE 43/01 ("43/01"), GELUCIRE 50/13 ("50/13"), and TEFOSE ("Tefose 63").

TABLE 1

| # | Vehicle system | Ratio | Physica state @ Room Temperature | Physical State @ 37° C. after ~30 minutes | Viscosity cps | Melting Time @ 37° C. | Dispersion in water 37° C. |
|---|---|---|---|---|---|---|---|
| 1 | MCM:39/01 | 8:2 | Solid | Clear liquid | 50 @ 37° C. | Start: 6 min Finish: 12 min | Small oil drops on top |
| 2 | MCM:39/01 | 7:3 | Solid | Clear liquid | | Start: 9 min Finish: 19 min | |
| 3 | MCM:39/01 | 6:4 | Solid | Clear liquid | | Start: 20 min Finish: 32 min | |
| 4 | MCM:43/01 | 8:2 | Solid | Liquid with solid particles | | | |
| 5 | MCM:43/01 | 7:3 | Solid | Liquid with solid particles | | | |
| 6 | MCM:50/13 | 9:1 | Liquid/cloudy | Liquid/cloudy | 140@25° C. | Clear after 20 min | Uniformly cloudy dispersion |

TABLE 1-continued

| # | Vehicle system | Ratio | Physical state @ Room Temperature | Physical State @ 37° C. after ~30 minutes | Viscosity cps | Melting Time @ 37° C. | Dispersion in water 37° C. |
|---|---|---|---|---|---|---|---|
| 7 | MCM:50/13 | 8:2 | Liquid/cloudy | Liquid/cloudy | 190@25° C. | | Uniformly cloudy dispersion |
| 8 | MCM:50/13 | 7:3 | Semisolid | Semisolid | | | |
| 9 | MCM:TEFOSE 63 | 9:1 | Semisolid | Liquid/cloudy | 150@25° C. | Start: 1 min Finish: 5 min | Uniformly cloudy dispersion |
| 10 | MCM:TEFOSE 63 | 7:3 | Semisolid | Semisolid | 240@25° C. | | Uniformly cloudy dispersion |
| 11 | MCM:TEFOSE 63 | 8:2 | Semisolid | Semisolid | 380@25° C. | Semisolid after 30 min at 37° C., doesn't melt at 41° C. | Uniformly cloudy dispersion |
| 12 | MIGLYOL 812: 50/13 | 9:1 | Semisolid | Semisolid | 140@25° C. | | 2 phases, oil on top |
| 13 | MIGLYOL 812: TEFOSE 63 | 9:1 | Liquid/cloudy | Liquid/cloudy | 90@25° C. | Start: 1 min Finish: 5 min | 2 phases, oil on top |

Vehicle systems in TABLE 1 that were liquid or semisolid at room temperature were tested using a Brookfield viscometer (Brookfield Engineering Laboratories, Middleboro, Mass.) at room temperature. Vehicle systems appearing in TABLE 1 that were solid at ambient temperature were tested using a Brookfield viscometer at 37° C.

Vehicle systems appearing in TABLE 1 that were solid were placed at 37° C. to assess their melting characteristics. The results are in TABLE 1. It is noted that vehicle system 11 in TABLE 1 did not melt at 37° C. or 41° C.

A dispersion assessment of the vehicle systems appearing in TABLE 1 was performed. The dispersion assessment was performed by transferring 300 mg of each vehicle system in 100 ml of 37° C. water, without agitation, and observing for mixing characteristics.

Example 2

Formulation: Gel Mass

In various embodiments, a vehicle system may be combined with a gel mass. A gel mass may comprise, for example, gelatin (e.g., Gelatin, NF (150 Bloom, Type B)), hydrolyzed collagen (e.g., GELITA®, GELITA AG, Eberbach, Germany), glycerin, SORBITOL SPECIAL® (a sorbitan-sorbitol based soft gel plasticizer), and/or other suitable materials in varying proportions. SORBITOL SPECIAL® may be obtained commercially and may tend to act as a plasticizer and humectant.

Gel masses A through F were prepared according to the formulations in TABLE 2. Gel masses A through F differ in the proportion of one or more components, for example.

TABLE 2

| Ingredient | Gel A % w/w | Gel B % w/w | Gel C % w/w | Gel D % w/w | Gel E % w/w | Gel F % w/w |
|---|---|---|---|---|---|---|
| Gelatin, NF (150 Bloom, Type B) | 41.0 | 41.0 | 41.0 | 41.0 | 43.0 | 43.0 |
| Glycerin 99.7%, USP | 6.0 | 6.0 | 6.0 | 6.0 | 18.0 | 18.0 |
| Sorbitol Special, USP | 15.0 | 15.0 | 15.0 | 15.0 | | |
| GELITA (hydrolyzed collagen) | 3 | | | | 3.0 | |
| Citric acid | | 0.1 | 0.5 | 1 | | 0.1 |
| Purifed Water | 35.0 | 37.9 | 37.5 | 37.0 | 36.0 | 38.9 |
| Total | 100.0 | 100.0 | 100.0 | 100.0 | 100.0 | 100.0 |
| Dissolution gel strips, Avg of 3 (500 ml DH2O, 50 rpm @ 37° C.) | 48 min (42, 45, 58) | 50 min (50, 51, 50) | 75 min (76, 75, 74) | 70 min (70, 71, 70) | | |
| Dissolution gel strips, Avg of 3 (500 ml pH 4 buffer, 50 rpm @ 37° C. | 70 min | | | | 72 min 84 min | 82 min |

Each gel mass A through F was prepared at a temperature range from about 45° C. to about 85° C. Each molten gelatin mass A through F was cast into a film, dried and cut into strips. The strips were cut into uniform pieces weighing about 0.5 g, with about 0.5 mm thickness. Strips were placed into a USP Type 2 dissolution vessel in either water or pH 4 buffer solution and the time for them to completely dissolve was recorded and listed in TABLE 2. It is noted that gel mass A has the fastest dissolution in both water and pH 4 buffer solution.

Example 3

Formulation: Final Formulation and Encapsulation

Various combinations of vehicle systems from TABLE 1 and gel masses from TABLE 2 were prepared. The combinations are shown in TABLE 3.

TABLE 3

| Trial | Vehicle system | Ratio | Batch Size g | Gel |
|---|---|---|---|---|
| 1 | MCM:39/01 | 8:2 | 750 | A |
| 2 | MCM:50/13 | 8:2 | 750 | A |
| 3 | MCM:TEFOSE 63 | 8:2 | 750 | A |
| 4 | MCM:TEFOSE 63 | 8:2 | 750 | B |
| 5 | MIGLYOL 812:TEFOSE 63 | 9:1 | 750 | A |

Estradiol was combined with each vehicle system so that about 10 mcg of estradiol was contained within 300 mg of each vehicle system. Batch size was as listed in TABLE 3. To encapsulate the vehicle system, each 300 mg of vehicle system was combined with about 200 mg of the listed gel mass. Thus, for example, in Trial 1, MCM:39/01 in an 8:2 ratio was combined with gel A and 10 mcg of estradiol. In each final dosage, Trial 1 comprised 300 mg of vehicle system, 200 mg of gel mass and 10 mcg of estradiol. It should be noted, however, that in various embodiments the total mass of vehicle system, gel mass, and estradiol may be from about 100 mg to about 1000 mg.

Each combination of vehicle system, estradiol, and gel mass may be suitable for use in, for example, a vaginal suppository.

Example 4

Estradiol Solubility

In various experiments, suitable solvents were determined for providing sufficient solubility to make 2 mg of estradiol in a 100 mg fill mass, with a desired goal of achieving ~20 mg/g solubility for estradiol. Initial solubility experiments were done by mixing estradiol with various solvents, saturate the solution with the estradiol, equilibrate for at least 3 days and filter the un-dissolved particles and analyzing the clear supernatant for the amount of estradiol dissolved by HPLC.

Estradiol solubility experiments were performed. From this list at least one item (e.g. propylene glycol) is known to be unsuitable for encapsulation.

TABLE 4

| Ingredient | Solubility (mg/g) |
|---|---|
| PEG 400 | 105* |
| Propylene Gylcol | 75* |
| Polysorbate 80 | 36* |

TABLE 4-continued

| Ingredient | Solubility (mg/g) |
|---|---|
| TRANSCUTOL HP | 141 |
| CAPMUL PG8 | 31.2 |

*Literature reference - Salole, E. G. (1987) The Physicochemical Properties of Oestradiol, J Pharm and Biomed Analysis, 5, 635-640

In further solubility studies, estradiol was soluble at least 6 mg/gm MIGLYOL TRANSCUTOL in ratios of 81:19 to 95:5, in MIGLYOL; ethanol at 91:11, and in MIGLYOL-CAPMUL PG8 at 88:11, but not in MIGLYOLTRANSCUTOL at 96:4, MIGLYOLLabrasol at 70:30 to 80:20, or MIGLYOLCAPMUL PG8 at 86:14.

Example 5

Process

With reference to FIG. 1, a method of making a fill material 100 is shown. Step 102 comprises heating a solubilizing agent to 40° C.±5° C. Heating may be accomplished through any suitable means. The heating may be performed in any suitable vessel, such as a stainless steel vessel. The solubilizing agent may be any such solubilizing agent described herein, for example, CAPMUL MCM.

Step 104 comprises mixing GELUCIRE with the solubilizing agent. As used herein, any form of GELUCIRE may be used in step 104. For example, one or more of GELUCIRE 39/01, GELUCIRE 43/01, GELUCIRE 50/13. may be used in step 104. Mixing may be facilitated by an impeller, agitator, or other suitable means. Step 104 may be performed under an inert or relatively inert gas atmosphere, such as nitrogen gas. Mixing may be performed in any suitable vessel, such as a stainless steel vessel.

Step 106 comprises mixing estradiol into the mixture of the solubilizing agent and GELUCIRE. The estradiol may be mixed in micronized or nonmicronized form. Mixing may occur in a steel tank or other acceptable container. Mixing may be facilitated by an impeller, agitator, or other suitable means. Step 106 may be performed under an inert or relatively inert gas atmosphere, such as nitrogen gas. In various embodiments, however, the addition of estradiol may be performed prior to step 104. In that regard, in various embodiments, step 106 is performed prior to step 104.

Step 110 comprises preparing the gel mass. Any of the gel masses described herein may be used in step 110. In that regard, gelatin (e.g., Gelatin, NF (150 Bloom, Type B)), hydrolyzed collagen, glyercin, and/or other suitable materials may be combined at a temperature range from about 45° C. to about 85° C. and prepared as a film. Mixing may occur in a steel tank or other acceptable container. Mixing may be facilitated by an impellor, agitator, or other suitable means. Step 110 may be performed under an inert or relatively inert gas atmosphere, such as nitrogen gas. Step 112 comprises degassing. The resulting mixture from step 112 may comprise a fill material suitable for production into a softgel capsule.

In step 112, a soft gel capsule is prepared by combining the material obtained in step 106 with the gel mass of step 110. The gel film may be wrapped around the material, partially or fully encapsulating it. The gel film may also be injected or otherwise filled with the material obtained in step 106.

Step 112 may be performed in a suitable die to provide a desired shape. Vaginal soft gel capsules may be prepared in a variety of geometries. For example, vaginal soft gel capsules may be shaped as a tear drop, a cone with frustoconical end, a cylinder, a cylinder with larger "cap" portion, or other shapes suitable for insertion into the vagina. Vaginal soft gel capsules in accordance with various embodiments may or may not be used in connection with an applicator.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. This disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad general meaning of the terms in which the appended claims are expressed. To the extent that these various modifications do not depart from the spirit and scope of the appended claims, they are intended to be encompassed therein.

What is claimed is:

1. A soft gelatin vaginal insert containing a fill material having a viscosity between 50 and 380 cP as measured at 25° C., the fill material comprising one or more C6 to C14 fatty acid mono-, di-, or triesters of glycerol, a nonionic surfactant comprising PEG-6 stearate, PEG-32 sterate, and ethylene glycol palmitostearate, and 1 to 10 mcg of estradiol,
    wherein estradiol is the only active ingredient in the vaginal insert;
    further wherein the insert is made by a process comprising:
    a) making a pre-fill material consisting essentially of:
        i. one or more C6 to C14 fatty acid mono-, di-, or triesters of glycerol;
        ii. a nonionic surfactant consisting essentially of PEG-6 stearate, PEG-32 stearate, and ethylene glycol palmitostearate; and
        iii. 1 to 10 mcg of estradiol;
    b) forming a soft gelatin capsule, and
    c) filling the soft gelatin capsule with the pre-fill material to make the insert.

2. The soft gelatin vaginal insert of claim 1, wherein the one or more C6 to C14 fatty acid mono-, di-, or triesters of glycerol is a C8 to C10 fatty acid triglyceride composition that is at least about 80% by weight caprylic (C8) acid and capric (C10) acids.

3. The soft gelatin vaginal insert of claim 1, wherein forming the pre-fill material comprises:
    a) optionally heating one or more C6 to C14 fatty acid mono-, di-, or triesters of glycerol;
    b) adding the nonionic surfactant to the one or more C6 to C14 fatty acid mono-, di-, or triesters of glycerol to form a mixture; and
    c) adding estradiol to the mixture.

4. The soft gelatin vaginal insert of claim 3, wherein heating is not optional.

5. The soft gelatin vaginal insert of claim 4, wherein heating comprises heating the one or more C6 to C14 fatty acid mono-, di-, or triesters of glycerol to a temperature ranging from about 35° C. to about 45° C.

6. The soft gelatin vaginal insert of claim 1, wherein the fill material contained within the soft gelatin capsule has a mass of about 300 mg.

7. The soft gelatin vaginal insert of claim 1, wherein the fill material comprises a 9:1 ratio of one or more C6 to C14 fatty acid mono-, di-, or triesters of glycerol and the to nonionic surfactant are present in a 9:1 ratio.

8. The soft gelatin vaginal insert of claim 6, wherein the fill material comprises a 9:1 ratio of one or more C6 to C14 fatty acid mono-, di-, or triesters of glycerol and the to nonionic surfactant are present in a 9:1 ratio.

9. The soft gelatin vaginal insert of claim 8, wherein the soft gelatin capsule consists essentially of 150 bloom, Type B gelatin, hydrolyzed collagen, glycerin, and, optionally, a sorbitan-sorbitol based soft gel plasticizer.

10. The soft gelatin vaginal insert of claim 8, wherein the fill material has a mass of about 300 mg.

11. The soft gelatin vaginal insert of claim 8, wherein the capsule has an interior wall surface defining an inner space, wherein a maximal length defined by two points on opposing sides of the interior wall surface is about 0.69 inches.

12. The soft gelatin vaginal insert of claim 8, wherein the capsule has an interior wall surface defining an inner space and an exterior wall surface disposed over the interior wall surface defining a thickness, wherein the thickness measured perpendicular to the interior wall surface and the exterior wall surface is about 0.108 inches.

13. The soft gelatin vaginal insert of claim 1, wherein the nonionic surfactant has an HLB value of less than about 10.

14. The soft gelatin vaginal insert of claim 1, wherein the nonionic surfactant has an HLB value of about 9 to about 10.

15. The soft gelatin vaginal insert of claim 1, wherein the insert is shaped with a wider bottom portion and a narrower top portion.

16. The soft gelatin vaginal insert of claim 1, wherein the vaginal insert is in the shape of a tear drop.

17. A soft gelatin vaginal insert consisting essentially of a soft gelatin capsule containing a fill material, the fill material consisting essentially of 1 to 10 mcg of estradiol and a solvent system, the solvent system consisting essentially of a 9:1 ratio of one or more C6 to C14 fatty acid mono-, di-, or triesters of glycerol to a nonionic surfactant consisting essentially of PEG-6 stearate, PEG-32 stearate, and ethylene glycol palmitostearate, wherein the fill material has a viscosity of between 50 and 380 cP as measured at 25° C.

18. A soft gelatin vaginal insert comprising a soft gelatin capsule containing a fill material, the fill material comprising 1 to 10 mcg of estradiol and a solvent system, the solvent system consisting essentially of a 9:1 ratio of (i) one or more C6 to C14 fatty acid mono-, di-, or triesters of glycerol to (ii) an excipient composition that does not increase the irritancy of the solvent system, the fill material having a viscosity of between 50 and 380 cP as measured at 25° C.

19. The soft gelatin vaginal insert of claim 18, wherein the excipient composition has an HLB value of less than about 10.

20. The soft gelatin vaginal insert of claim 19, wherein the excipient composition has an HLB value of about 9 to about 10.

21. The soft gelatin vaginal insert of claim 19, wherein the insert is shaped with a wider bottom portion and a narrower top portion.

22. The soft gelatin vaginal insert of claim 19, wherein the vaginal insert is in the shape of a tear drop, a cone with a frustoconical end, or a cylinder with a wider cap portion.

* * * * *